US011324698B2

United States Patent
Konduri et al.

(10) Patent No.: US 11,324,698 B2
(45) Date of Patent: May 10, 2022

(54) STERICALLY STABILIZED CARRIER FOR AEROSOL THERAPEUTICS, COMPOSITIONS AND METHODS FOR TREATING THE RESPIRATORY TRACT OF A MAMMAL

(71) Applicant: VGSK Technologies, Inc., Madison, WI (US)

(72) Inventors: Kameswari S. Konduri, Madison, WI (US); Sandhya N. Nandedkar, Brookfield, WI (US); Nejat Duzgunes, Mill Valley, CA (US); Pattisapu Ram Jogi Gangadharam, Irving, TX (US)

(73) Assignee: VGSK Technologies, Inc., Madison, WI (US)

( * ) Notice: Subject to any disclaimer, the term of this patent is extended or adjusted under 35 U.S.C. 154(b) by 0 days.

(21) Appl. No.: 16/856,349

(22) Filed: Apr. 23, 2020

(65) Prior Publication Data
US 2020/0352859 A1 Nov. 12, 2020

Related U.S. Application Data

(63) Continuation of application No. 14/453,125, filed on Aug. 6, 2014, now abandoned, which is a (Continued)

(51) Int. Cl.
*A61K 9/127* (2006.01)
*A61K 9/00* (2006.01)
(Continued)

(52) U.S. Cl.
CPC .......... *A61K 9/1271* (2013.01); *A61K 9/0073* (2013.01); *A61K 9/127* (2013.01);
(Continued)

(58) Field of Classification Search
CPC .............. A61K 9/1271; A61K 38/1709; A61K 31/573; A61K 31/7032; A61K 38/482;
(Continued)

(56) References Cited

U.S. PATENT DOCUMENTS 5,013,556 A 5/1991 Woodle et al.
5,356,633 A 10/1994 Woodle et al.
(Continued)

OTHER PUBLICATIONS

Ajay Kumar Thakur et al., "Patented therapeutic drug delivery strategies for targeting pulmonary diseases", Expert Opinion on Therapeutic Patents, 2020, 1744-7674.
(Continued)

*Primary Examiner* — Gollamudi S Kishore
(74) *Attorney, Agent, or Firm* — Wilson Sonsini Goodrich & Rosati

(57) ABSTRACT

The application disclosure provides a sterically stabilized liposome carrier encapsulating a selected drug for the aerosol delivery of the drug effectual in the treatment of a mammal, a composition containing the sterically stabilized liposome carrier and the selected drug effective for the treatment of airway hypersensitivity and inflammation such as of the lungs of a mammal as an aerosol, and a method of treatment using the composition. The composition disclosed herein provides effective treatment for the longer of a period of time at least twice as long as the selected drug alone or up to at least one week.

17 Claims, 29 Drawing Sheets

Related U.S. Application Data continuation of application No. 12/218,777, filed on Jul. 18, 2008, now Pat. No. 8,846,079, which is a continuation-in-part of application No. 11/287,703, filed on Nov. 22, 2005, now abandoned, said application No. 12/218,777 is a continuation-in-part of application No. 10/769,034, filed on Jan. 30, 2004, now abandoned.

(60) Provisional application No. 60/632,181, filed on Dec. 1, 2004, provisional application No. 60/498,609, filed on Aug. 28, 2003, provisional application No. 60/498,546, filed on Aug. 28, 2003.

(51) Int. Cl.

| | | |
|---|---|---|
| *A61K 31/7032* | (2006.01) | |
| *A61K 31/573* | (2006.01) | |
| *A61K 31/58* | (2006.01) | |
| *A61K 31/7028* | (2006.01) | |
| *A61K 38/17* | (2006.01) | |
| *A61K 38/48* | (2006.01) | |

(52) U.S. Cl.
CPC .......... *A61K 31/573* (2013.01); *A61K 31/58* (2013.01); *A61K 31/7028* (2013.01); *A61K 31/7032* (2013.01); *A61K 38/1709* (2013.01); *A61K 38/482* (2013.01); *C12Y 304/2102* (2013.01)

(58) Field of Classification Search
CPC ...... A61K 9/0073; A61K 9/127; A61K 31/58; A61K 31/7028; C12Y 304/2102
See application file for complete search history.

(56) References Cited

U.S. PATENT DOCUMENTS

| | | | |
|---|---|---|---|
| 5,824,761 A | 10/1998 | Bujanowski et al. | |
| 5,891,468 A | 4/1999 | Martin et al. | |
| 5,958,378 A | 9/1999 | Waldrep et al. | |
| 6,197,333 B1 | 3/2001 | Onyuksel et al. | |
| 6,203,822 B1 | 3/2001 | Schlesinger et al. | |
| 6,461,591 B1 | 10/2002 | Keller et al. | |
| 6,562,371 B1 | 5/2003 | Kawahara et al. | |
| 6,566,324 B2 | 5/2003 | Nadel et al. | |
| 6,660,525 B2 | 12/2003 | Martin et al. | |
| 6,824,761 B1 | 11/2004 | Hills et al. | |
| 8,846,079 B1 | 9/2014 | Konduri et al. | |
| 2002/0009488 A1* | 1/2002 | Francis | A61K 9/1271 424/450 |
| 2002/0106330 A1 | 8/2002 | Waldrep et al. | |
| 2002/0110587 A1 | 8/2002 | Rodrigueza et al. | |
| 2002/0131995 A1 | 9/2002 | Szoka, Jr. | |
| 2002/0156062 A1 | 10/2002 | Boch et al. | |
| 2003/0147945 A1* | 8/2003 | Tardi | A61K 31/7076 424/450 |
| 2004/0076691 A1 | 4/2004 | Haines et al. | |
| 2004/0097471 A1 | 5/2004 | Maring et al. | |
| 2004/0110695 A1* | 6/2004 | Dobbie | A61P 35/00 514/44 R |

OTHER PUBLICATIONS

Gangadharam, et al. Therapy of *Mycobacterium avium* Complex Infections in Beige Mice With Streptomycin Encapsulated in Sterically Stabilized Liposomes. Antimicrobial Agents and Chemotherapy, 39(3):725-730 (1995).

Konduri, et al. Budesonide Delivered in Sterically Stabilized Liposomes Decreases Airway Hyperresponsiveness to Methacholine. Presented at the Annual AAAAI Meeting, Denver, CO., Mar. 2003. 19 pages.

Konduri, et al. Efficacy of Liposomal Budesonide in Experimental Asthma abstract presented at the Annual AAAAI meeting, New Orleans, LA, 2001. Published in Journal of Allergy Clinical Immunology, vol. 111, No. 2, 2003. 7 pages.

Konduri, et al. Efficacy of Liposome Encapsulated Budesonide in Experimental Asthma. Abstract 1029. Journal of Allergy Clinical Immunology. vol. 107, No. 2, Feb. 2001. 1 page.

Notice of Allowance dated May 16, 2014 for U.S. Appl. No. 12/218,777.

Office Action dated Feb. 8, 2017 for U.S. Appl. No. 14/453,125.

Office Action dated Apr. 18, 2011 for U.S. Appl. No. 12/218,777.

Office Action dated Aug. 22, 2017 for U.S. Appl. No. 14/453,125.

Office Action dated Aug. 23, 2011 for U.S. Appl. No. 12/218,777.

Office Action dated Sep. 11, 2013 for U.S. Appl. No. 12/218,777.

Schreier, Hans. Pulmonary applications of liposomes. Medical Applications of Liposomes. D.D. Lasic and D. Papahadjopoulos. 1998. Chapter 6.3. pp. 474-475. 4 pages.

Upendra Bulbake et al., "Liposomal Formulations in Clinical Use: An updated Review", Pharmaceutics, 2017, 9, 12, pp. 1-33.

U.S. Appl. No. 14/453,125 Office Action dated Apr. 5, 2018.

* cited by examiner

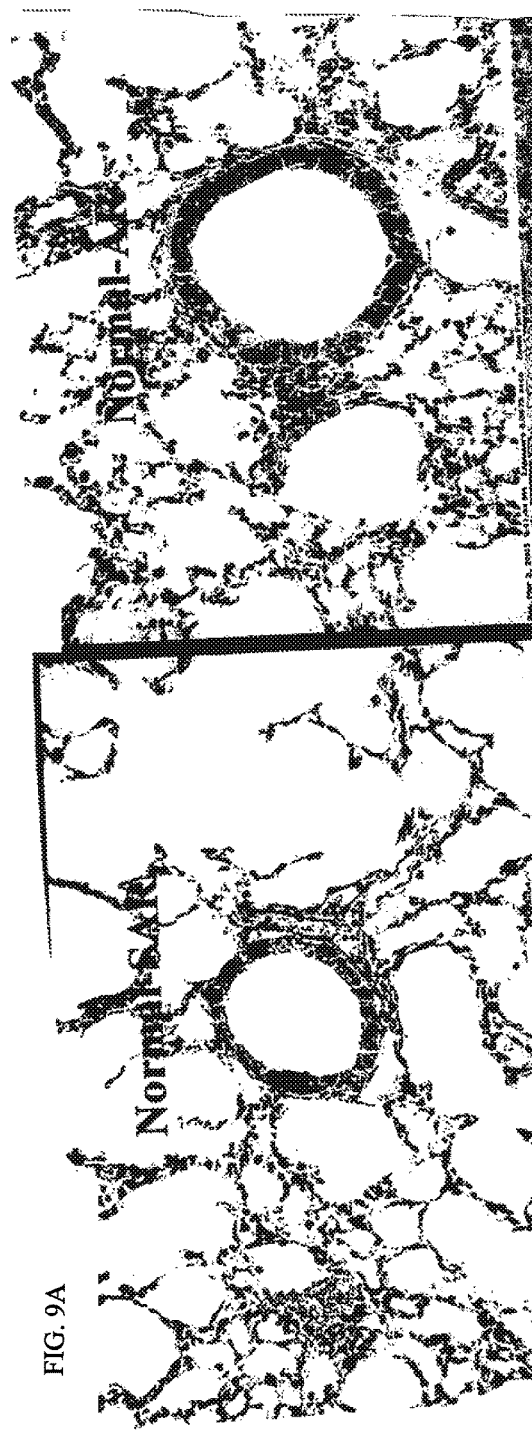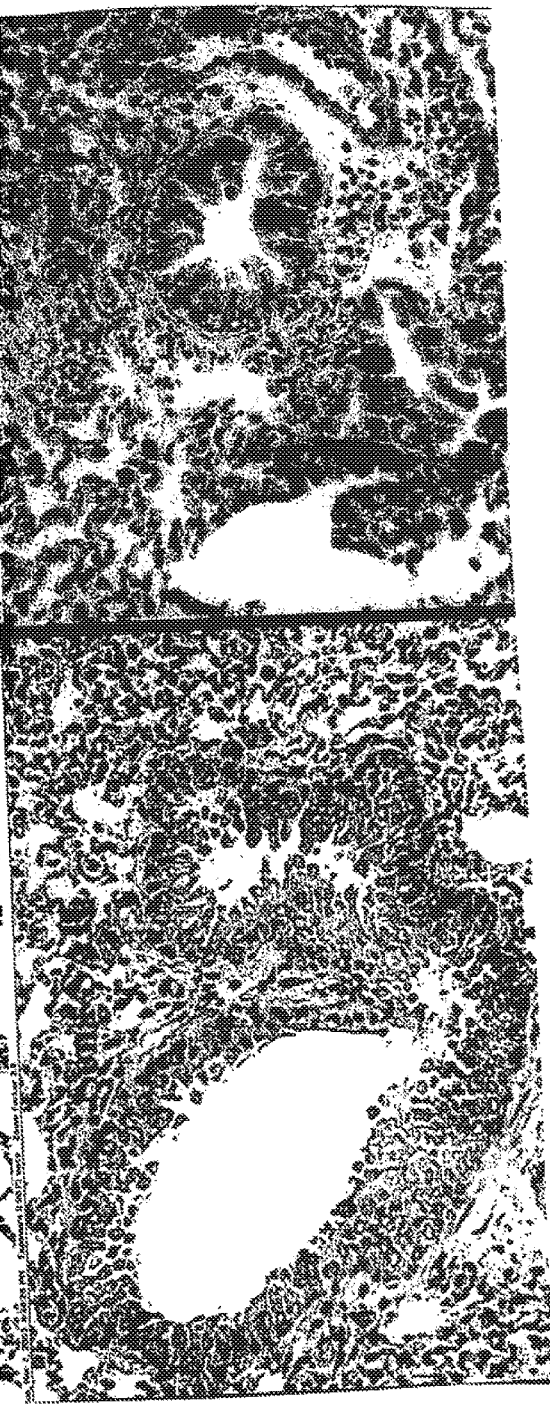
FIG. 9A  FIG. 9B  FIG. 9C  FIG. 9D

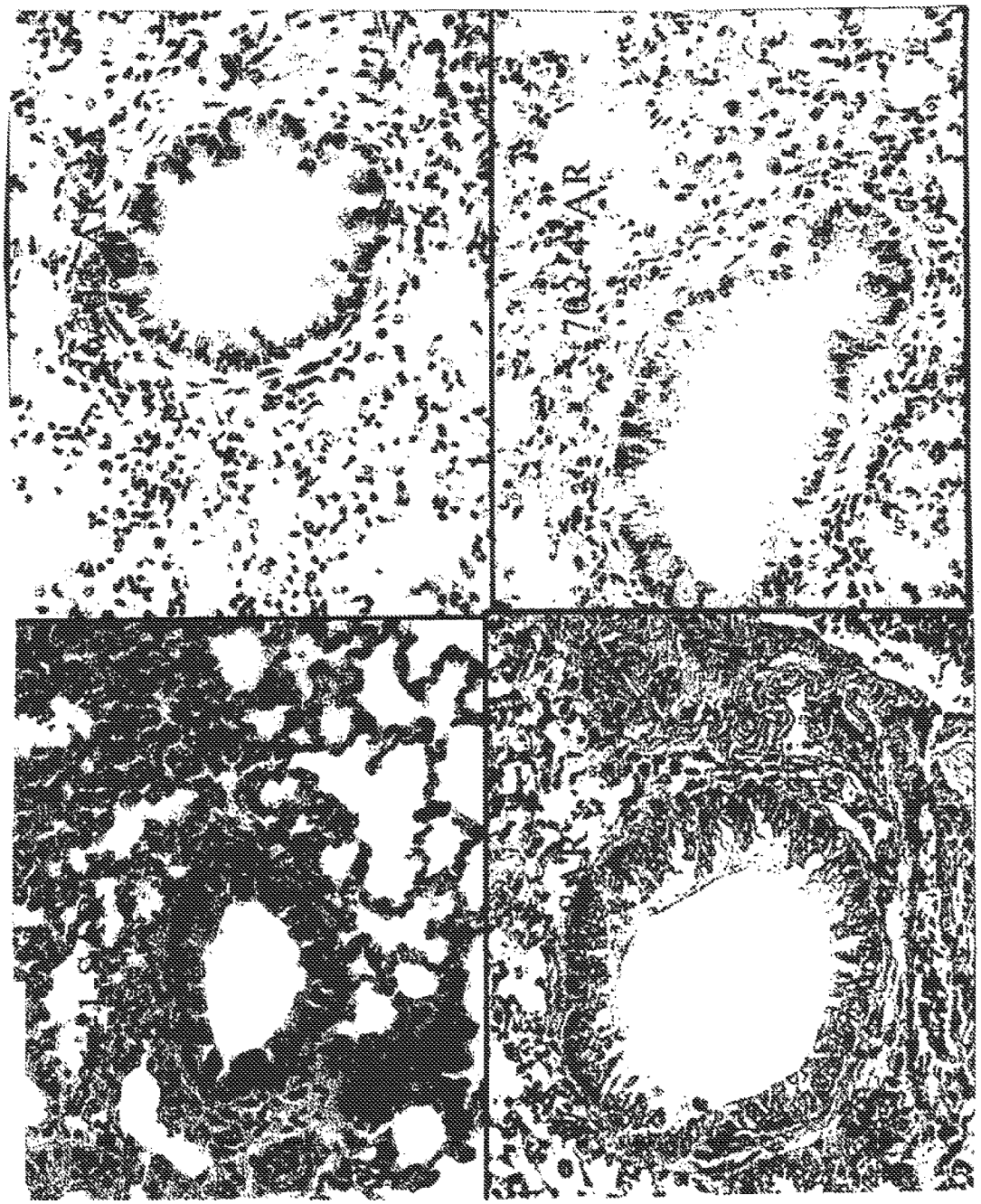

Sterically Stabilized Liposomes = SSL

Sterically Stabilized Liposomes = SSL

STERICALLY STABILIZED CARRIER FOR AEROSOL THERAPEUTICS, COMPOSITIONS AND METHODS FOR TREATING THE RESPIRATORY TRACT OF A MAMMAL

RELATED CASES

This application is a continuation of U.S. Ser. No. 14/453,125 filed Aug. 6, 2014, which is a continuation of U.S. Ser. No. 12/218,777 filed Jul. 18, 2008 which is continuation-in-part of U.S. Ser. No. 11/287,703 filed Nov. 22, 2005 which is entitled to and claims the benefit of the filing date of U.S. provisional application No. 60/632,181 filed Dec. 1, 2004; and of U.S. Ser. No. 10/769,034 filed Jan. 30, 2004 which is entitled to and claims the benefit of the filing dates of U.S. Provisional Nos. 60/498,609 and 60/498,546, both filed Aug. 28, 2003.

FIELD OF THE INVENTION

This invention is directed to a sterically stabilized liposome carrier effective for the aerosol delivery of a drug effectual in the treatment of a mammal, a composition comprising the sterically stabilized liposome carrier and a drug effective for the treatment of a mammal which is administered via the respiratory tract of a mammal as an aerosol and a method of treatment using the composition. The composition provides, with one dose, effective treatment for the longer of a period of time twice as long as the effective time for aerosol treatment of the mammal with a comparable quantity of the drug alone or up to at least seven days.

BACKGROUND OF THE INVENTION

Asthma is a common disease that causes recurrent symptoms, repeated hospitalizations and an increased risk of sudden death. It is the most common childhood illness and affects 20 million Americans. According to the American Academy of Allergy, Asthma & Immunology, asthma causes direct health care costs in the United States of over $11.5 billion annually. Additionally, in the United States lost productivity adds another $4.6 billion and drugs prescribed for asthma patients represent costs of over $5 billion annually.

Asthma is characterized by acute bronchial constriction, chronic lung inflammation and airway hyperreactivity which results in chronic inflammation and airway remodeling that leads to progressive and possibly irreversible airway damage. The most effective therapy focuses on the early stages of the disease before the vicious cycle of inflammatory changes can become irreparable. The disease usually starts in early childhood and most commonly before five years of age. Thus, appropriate management of asthma in childhood may have a greater impact on the course of the disease than interventions later in life.

The mainstay of asthma treatment therapy is the use of anti-inflammatory drugs (i.e., inhaled corticosteroids). As a first line therapy for patients above five years of age, inhaled corticosteroids are usually given via an inhaler twice a day. Patients under five years of age are frequently given a nebulized form of budesonide (BUD), which is a potent inhaled corticosteroid, given twice a day as a first line therapy.

Although inhaled corticosteroids are very effective in preventing the massive inflammation that occurs with asthma, they do have some major drawbacks. One is that these drugs must be given at least daily to be effective. For instance, the effective life of BUD alone in the lungs is no more than one day. This daily dosage requirement may lead to non-adherence by the patient. Since adherence to daily use of inhaled corticosteriods by the patient is critical in interrupting the chronic inflammation that occurs in asthma, this becomes a focal issue for effective therapy. Further the effective use of an inhaler is very technique-dependent. Typically only up to about fifteen percent of a given dose is delivered to the lungs using an inhaler. The inhaled corticosteroids have a short half-life in the body and have potential toxicity when used in higher doses. These are serious disadvantages to the use of corticosteroid drugs in conventional therapy.

In an abstract published by the present inventors in the Journal of Allergy Clinical Immunology entitled "Efficacy of Liposome Encapsulated Budesonide in Experimental Asthma," February, 2001, Vol. 107, No. 2, it is disclosed that BUD encapsulated in sterically stabilized liposomes prevents asthma inflammation in lower doses given at less frequent dosing intervals by comparison to daily BUD therapy. Test results are summarized demonstrating an improvement. The abstract does not disclose a suitable sterically stabilized liposome, suitable types of sterically stabilized liposomes or any method for producing a suitable sterically stabilized liposome, for producing BUD encapsulated in a suitable sterically stabilized liposome or a method for administering the sterically stabilized liposome containing BUD.

In view of the likelihood of possible adverse effects with use of corticosteroids and the frequency with which the corticosteroids and other drugs are required, a continued effort has been directed to the development of improved techniques for administering a drug to a mammal via the respiratory tract of the mammal so that it may be administered more effectively and so that the effectiveness of the drug can be achieved using smaller doses and at less frequent dosing intervals.

SUMMARY OF THE INVENTION

The present invention comprises a composition consisting essentially of a sterically stabilized liposome carrier having a gel-liquid transition temperature from about −20° C. to about 44° C. and encapsulating a selected drug effective for aerosol administration to the respiratory tract of a mammal, the sterically stabilized liposome carrier comprising phosphatidylcholine, phosphatidylglycerol and poly(ethylene glycol), the composition being of a particulate size up to about 0.2 to about 5.0 microns and the effective to result in deposit of the selected drug in the airways down to the alveoli and alveolar tight junction upon inhalation of the composition by the mammal and providing an effective life for the selected drug in a mammal equal to at least twice the effective life, or up to a week, of a single dose of the selected drug alone.

The invention further comprises a method for treating a mammal with a selected drug by forming an aerosol of a composition consisting of a sterically stabilized liposome carrier encapsulating an effective amount of the selected drug effective for treatment of the mammal. The sterically stabilized liposome comprising phosphatidylcholine, phosphatidylglycerol, and poly(ethylene glycol), the composition being of a particulate size up to about 0.2 to about 5.0 microns and effective to result in deposit of the selected drug in the airways down to the alveoli and alveolar tight junction having a gel-liquid transition temperature from about −20° C. to about 44° C. and providing an effective life for the drug in the respiratory tract of a mammal equal to at least twice the life of a single dose, or up to a week, of the selected drug alone; and, allowing the mammal to inhale an effective amount of the aerosol at selected time intervals.

The invention further comprises a method for treating a mammal with a selected drug by forming an aerosol of a carrier consisting essentially of a sterically stabilized liposome carrier encapsulating the selected drug effective for treatment of the respiratory tract of a mammal. The sterically stabilized liposome carrier consists essentially of phosphatidylcholine and poly (ethylene glycol), the composition providing an effective life for the drug in the respiratory tract of a mammal equal to at least twice the effective life or up to a week of a single dose of the selected drug alone; and, allowing the mammal to inhale an effective amount of the aerosol at selected time intervals.

The invention also comprises a method for treating a mammal with a selected drug by forming an aerosol of a composition consisting of a sterically stabilized liposome carrier encapsulating an effective amount of a selected drug effective for treatment of the mammal. The sterically stabilized liposome carrier consists essentially of phosphatidylglycerol and poly (ethylene glycol), the composition providing an effective life for the drug in the respiratory tract of a mammal equal to at least twice the effective life, or up to a week, of a single dose of the selected drug alone; and, allowing the mammal to inhale an effective amount of the aerosol at selected time intervals.

BRIEF DESCRIPTION OF THE DRAWINGS

FIGS. 9A-9L and 10-15 show graphical and pictorial presentations of the use of BUD encapsulated in the carrier with and without cholesterol on lung inflammation and AHR for the mice groups tested in BUD 3;

DESCRIPTION OF PREFERRED EMBODIMENTS

Figure 1:
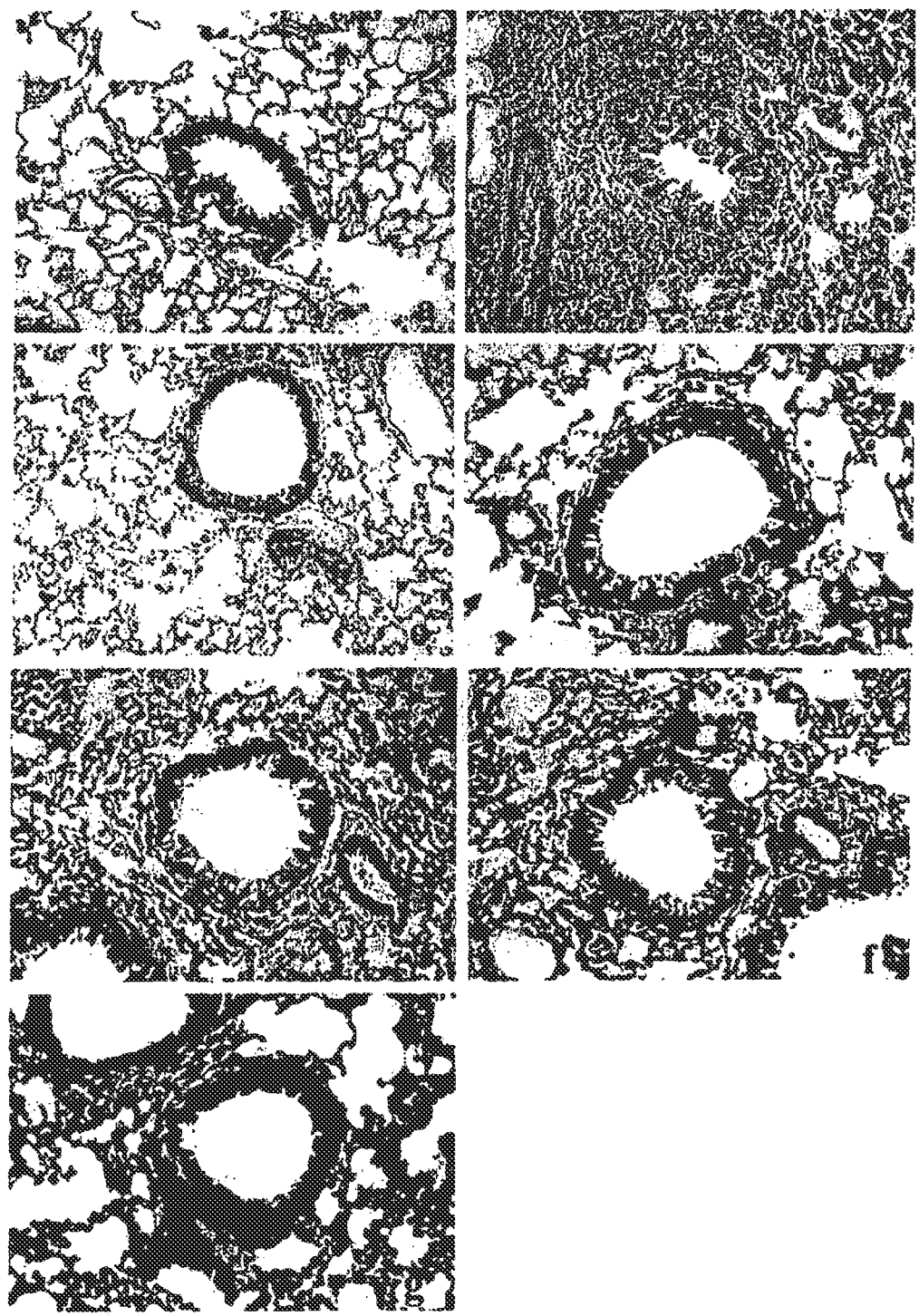
FIGS. 1-5 show graphical and pictorial presentations of a comparison of the use of BUD encapsulated in the carrier to the use of BUD encapsulated in the conventional carrier on lung inflammation for the mice groups listed in BUD 1.

Liposomes are well known materials that comprise primarily phospholipid bilayered vesicles of many types that can encapsulate a variety of drugs and some types are avidly phagocytosed by macrophages in the body. The various interactions of the liposomes can be generalized into four categories: (1) exchange of materials, including lipids, lipids and proteins with cell membranes or transfer of encapsulated drugs to the cell; (2) absorption or binding of liposomes to cells; (3) cell internalization of liposomes by endocytosis or phagocytosis once bound to the cell; and, (4) fusion of bound liposomes with the cell membrane. In all these interactions, there is a strong dependence on lipid composition, type of cell, presence of specific receptors and many other parameters.

Liposomes have been used to provide drugs in mammals, particularly when it is desired to apply the drugs to specific areas for specific applications. Liposomes have been used to encapsulate antibiotics, antiviral agents and the like and have been shown to enable enhanced efficacy against a variety of infectious diseases. A major drawback of conventional liposomes is that they have a relatively short life in a mammal body. Most applications have used liposomes in the bloodstream.

To extend the life of liposomes in a mammal body, attempts have been made to develop sterically stabilized liposomes, which have a longer life in a mammal body. Attempts to extend the life of liposomes have included the use of poly(ethylene glycol), natural glycolipids, surfactants, polyvinyl alcohol, polylactic acid, polyglycolic acid, polyvinyl pyrrolidene, polyacrylamine and other materials in various combinations with the liposomes in attempts to provide sterically stabilized liposomes, which are effective for drug delivery and which are compatible with a mammal circulatory system. The most prominent sterically stabilized liposomes utilize distearoylphosphatidylcholine as the primary phospholipid.

Liposome-encapsulated antibiotics show increased efficacy for treatment of a variety of infectious diseases. Liposomes have also been considered for the delivery of aerosolized asthma medications, such as chromolyn sodium and albuterol sulfate. However the potential role of liposome encapsulation in enhancing the efficacy of inhaled steroid preparations used in asthma remained unknown at the time of this invention.

Liposomes are characterized by their lipid composition, surface charge, steric interactions and number of lamellae. Conventional liposomes are composed of naturally-occurring phospholipids, such as phosphatidylglycerol and phosphatidylcholine mixed with or without cholesterol. Although conventional liposomes can encapsulate a variety of drugs, they are recognized in vivo by the cells of the reticuloendothelial system and are cleared rapidly from the circulation. In addition, incorporation of triamcinolone (TRI) or beclomethasone into conventional liposomes results in their rapid redistribution and leakage from liposomes into the medium.

In contrast to conventional liposomes, sterically stabilized liposomes exhibit increased stability in plasma and decreased uptake by the reticuloendothelial system. Although several studies have reported the use of conventional liposomes in asthma therapy, sterically stabilized liposomes have not been investigated as a carrier for the delivery of anti-inflammatory or other drugs by aerosol administration to the respiratory tract of a mammal. For conciseness the present invention has been discussed and its efficacy shown by treatment of a respiratory tract of a mammal for asthma, although the invention is not limited to asthma treatment or drugs for treatment of the respiratory tract.

For use in the present invention, it has been necessary to produce sterically stabilized liposomes which are compatible with a mammal respiratory system and lungs, adapted for aerosol administration to the mammal and which have an extended life in the lungs, respiratory tract and bloodstream. Thus conventional liposomes are not functional for the purpose of treating the respiratory tract of a mammal for the applications discussed in this application.

A property of the carriers of the present invention is that the carriers are uniquely adapted for use in the lungs. They have the ability to not disrupt the composition and function of lung surfactant which provides a lateral surface pressure in the lungs which prevents lung collapse. Thus an ideal mixture of lipids in the sterically stabilized liposomes will be one closest to that of lung surfactant lipids. One such lipid composition is DPPC:DPPG:PEG-DSPE (80:15:5). An alternative lipid composition is DPPC:DPPG:PEG-DSPE (78:18:4). DPPC is an abbreviation for dipalmitoylphosphatidylcholine. DPPG is an abbreviation for dipalmitoylphosphatidylglycol. PEG is an abbreviation for poly(ethylene glycol). DPPE is an abbreviation for distearoylphosphatidylethanolamine. The ratios are expressed as molar ratios.

Properties of the carrier of the present invention uniquely adapted to retain the drug for long periods of time are: (1) its composition which facilitates the encapsulation of a drug within the bilayer or inside the carrier; (2) the presence of sufficient amounts of PEGylated (PEG refers to poly(ethylene glycol)) lipids to stabilize and protect the liposome from disruption upon exposure to biological milieu, including lung surfactant and lung surfactant proteins and upon nebulization; and, (3) the presence of an amount of PEGylated lipid sufficient to enable the drug to remain liposome-associated for a long enough period to be effective in the lungs.

The sterically stabilized liposomes of the carriers have a composition such that they are readily administered to the mammal as an aerosol and will remain stable in the presence of serum and in the extra-cellular environment. They preferentially localize to the lungs, especially to areas of inflammation as commonly seen in asthma, i.e., in lung inflammation and in the airway hypersensitivity response. A suitable way to administer the composition of the present invention is via an aerosolization, such as nebulizer. These sterically stabilized liposomes are amenable to nebulization. The combination of these sterically stabilized liposomes with encapsulated drugs useful in the treatment of mammalian respiratory tract diseases has been shown herein with corticosteroids: BUD and TRI; monophosphoryl lipid A (MPL); peptides: D-4F (apol lipoprotein A-1 mimetic) and Serine Lung Protease Inhibitor (SLPI) for the treatment of lung inflammation and airway hyper-responsiveness.

It is anticipated that these sterically stabilized liposome carriers will also be effective for the delivery of a wide variety of drugs for the treatment of respiratory and other diseases. The stability of the sterically stabilized liposomes in combination with the encapsulated drug is more pronounced than currently available drug therapies. As demonstrated in the following examples, this stability may allow a drug, such as a corticosteroid, to be administered only once every one to two weeks. The dosage used in these treatments is typically the same or similar to that used on a daily basis. The drug may thus be administered at two, three, four, five, six or seven days or longer intervals. In some instances, the effective life may be up to two weeks or longer. The effective life of the drug in the respiratory tract has thus been extended to the longer of at least twice the life of the drug alone, or at least one week, thus reducing the amount of the drug required to one-seventh of the previously required dosage. The term "effective life" as used herein means a period during which the drug effect is continued. Sustained action of the drug has been obtained at comparable initial dosages with a reduction in toxicity using the carrier. No suggestion or any enabling disclosure or data in the prior art is known that extended drug life could be obtained with these sterically stabilized liposome carriers for aerosol drug treatments for asthma or any other disease, particularly for lung inflammation and airway hyper-responsiveness. The extended drug life has not been obtained with the administration of the free drug and free carrier given simultaneously but without encapsulation.

The drugs can be of a wide variety, such as D-4F, which is a known anti-inflammatory cardiovascular drug for cardiovascular diseases whose efficacy with the carrier of the present invention has been shown in the Examples for use in a mammalian respiratory tract. The drug in combination with the sterically stabilized liposomes has been shown to enter the alveoli from which oxygen is passed to the blood. It is considered that the drug encapsulated in the carrier is also passed through the tight junction from the alveoli into the blood stream as is the oxygen. The sterically stabilized liposomes are relatively stable in the blood stream and provide extended drug life for the encapsulated drug.

The sterically sterilized liposome carriers of the present invention, which are adapted for combination with a variety of drugs for use in the aerosol treatment of a respiratory tract in a mammal, comprise sterically stabilized liposomes that are compatible with the respiratory tract of a mammal and which are effective to extend the effective life of the drug in the respiratory tract by a time equal to the longer of at least twice the effective life of the drug alone, or at least one week. The sterically stabilized liposome carriers of the present invention are tailored to be compatible with naturally occurring fluids and surfactant found in the lung and the liposome carriers have been observed to bind to Type 2 pneumocytes in the lungs. The carrier is tailored to accommodate the surfactant found in the lungs so that the compositions of the sterically stabilized liposome carriers of the present invention are similar to lung surfactant and provide long stability to the alveoli and the respiratory tract when used to encapsulate drugs and have been found to be effective to extend the effective life of the drugs administered.

Figure 38:
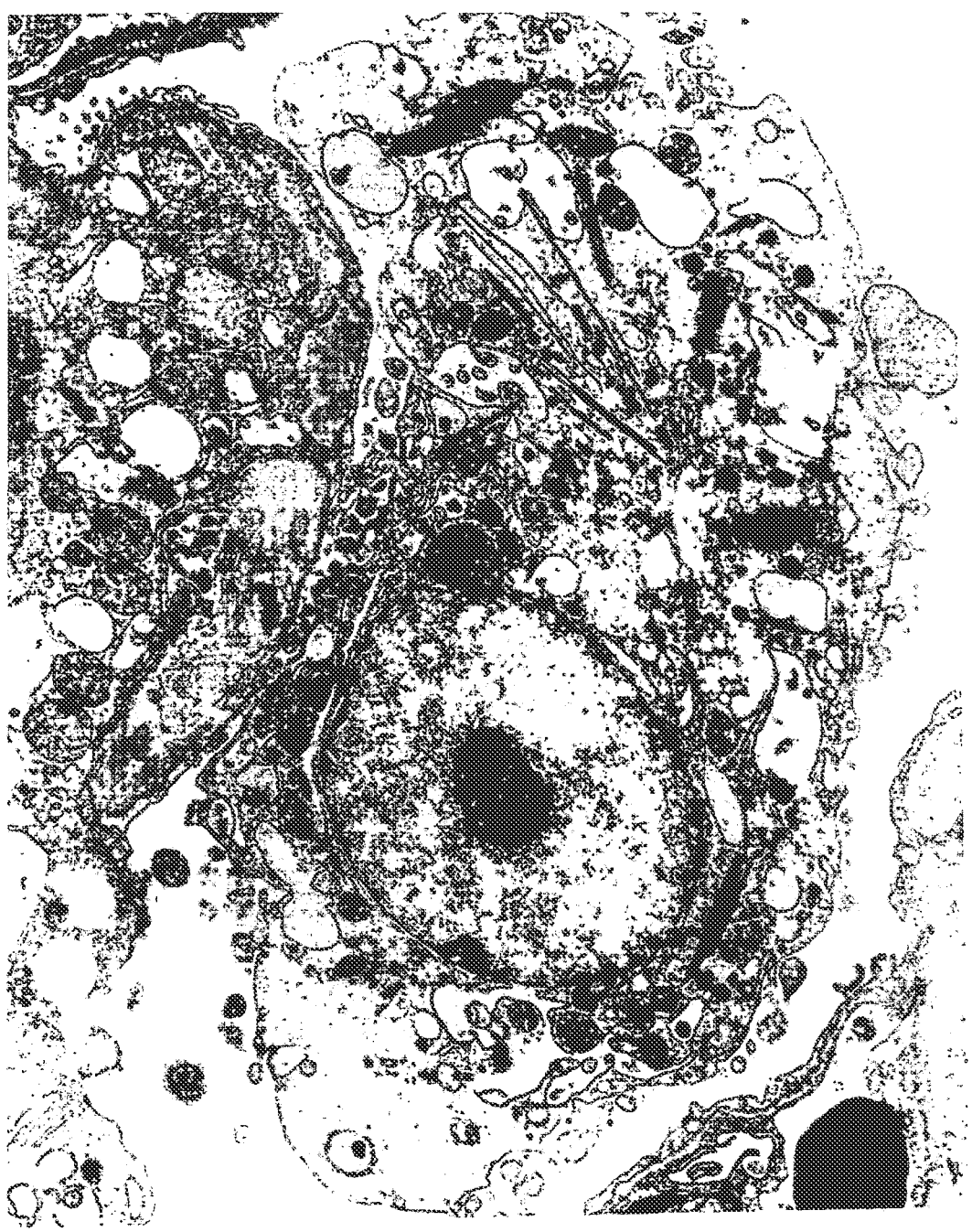
FIGS. 38-40 show pictures of Electron Microscopy of lung tissues with the BUD encapsulated in the carrier in comparison with BUD encapsulated in the conventional carrier in EM.
Figure 40:
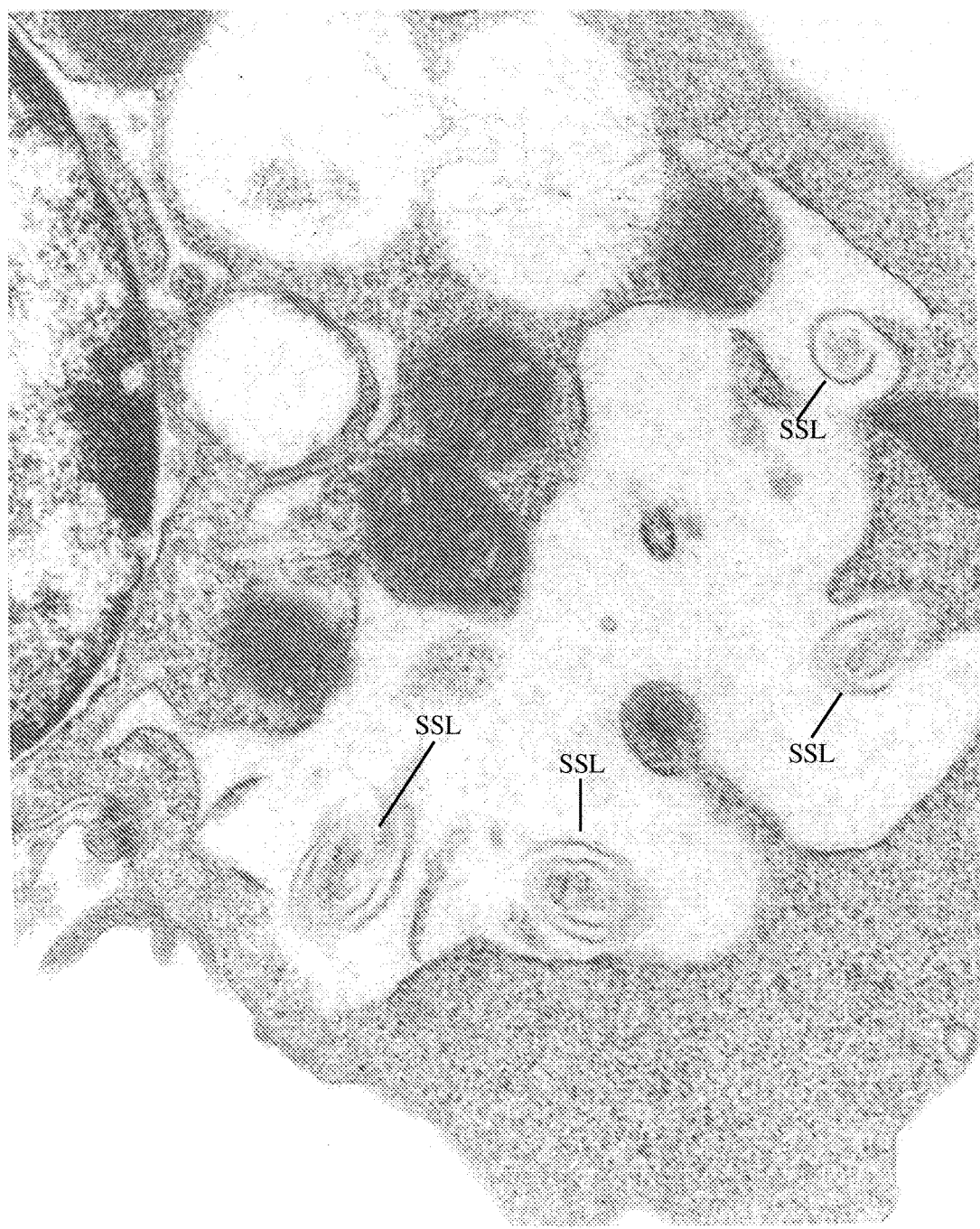

The carriers have wide applicability for use in the respiratory tract of a mammal. As shown in the examples, by electronmicroscopy observations, it has been observed that the carrier which encapsulates the drug is not destroyed in the lungs rapidly and is deposited in the cells around the alveoli in the lung tissues (FIGS. 38 and 40). These Figures show that the carrier particles bearing the drug pass through the lung airways down to the alveoli and the alveolar tight junctions. Since the carrier encapsulating the drug is deposited in the lung tissues, the encapsulated drug has the same medicinal effect as usual but since it is encapsulated in the carrier deposited in the lung tissues, it is released more slowly, thus providing a long-term effect. Any drug which can be encapsulated in the carrier is considered to provide the same long-term effect in the respiratory tract or in the bloodstream. In the examples it is shown that this effect has been achieved with corticosteroids: BUD and TRI; monophosphoryl lipid A (MPL); peptides: D-4F (apol lipoprotein A-1 mimetic) and Serine Lung Protease Inhibitor (SLPI) for the treatment of lung inflammation and airway hyper-responsiveness. All of these drugs when encapsulated and tested in a mammal as shown have given the extended effective treatment life. Further conventional liposomes, by comparison to sterically stabilized liposomes, do not provide an extended drug life. Secondarily, the drug rapidly leaks out from the conventional liposomes.

The sterically stabilized liposome carriers of the present invention comprise phosphatidylcholine or phosphatidylglycerol and poly (ethylene glycol) or both phosphatidylcholine and phosphatidylglycerol with poly (ethylene glycol). The phosphatidylcholine and phosphatidylglycerol may be synthetically derived or they may be derived from chicken eggs or soybeans. If derived from eggs they contain acyl groups having varying numbers of carbon atoms, dependent upon the variety and diet of the chicken that produces the eggs. The phosphatidylcholine is typically present in a relatively significant quantity in the combination of sterically stabilized liposomes.

A further component of the sterically stabilized liposome carriers is poly(ethylene glycol), in the molecular range from about 500 to above 5,000 daltons. The poly(ethylene glycol) may be present in combination with phosphatidylcholine, phosphatidylglycerol and lipids which may include amino or other groups.

Any of the head groups (phosphatidylcholine and phosphatidylglycerol) or the poly(ethylene glycol), may be attached to acyl groups containing from about 8 to about 18 carbon atoms. Preferably, from about 14 to about 18 carbon atoms are present in the acyl groups. Such groups comprise distearoyl, stearoyl oleoyl, stearoyl palmitoyl, dipalmitoyl, dioleoyl, palmitoyl oleoyl and dipalmitoleoyl.

If shorter chains are used, such as palmitoyl, dimyristoyl, didodecanoyl, didecanoyl or dioctanoyl, the poly(ethylene glycol)-lipid is likely to exchange into biological milieu. This may in some instances permit the sterically stabilized liposome carrier to better partition onto lung surfactant after sustained shedding or sustained exchanging its poly(ethylene glycol) moiety.

Desirably, the sterically stabilized liposome carriers may be tailored to the particular mammalian lung system contemplated. It is considered, however, that such sterically stabilized liposome carriers will fall within the criteria defined above and hereinafter for the liposomes.

The sterically stabilized liposomes may contain at least one or both of phosphatidylcholine and phosphatidylglycerol, and poly (ethylene glycol) distearoylphosphatidyldiethanolamine, lipid conjugated polyoxyethylene, lipid conjugated polysorbate, or lipids conjugated to other hydrophilic steric coating molecules safe for in vivo use.

A particularly preferred carrier is phosphatidylcholine, phosphatidylglycerol, poly (ethylene glycol) distearoylphosphatidyldiethanolamine (PEG-DSPE).

The molecular weight of the phosphatidylcholine is desirably from about 509 to about 791, preferably from about 677 to about 791 and more preferably from about 734 to about 791. The molecular weight of the phosphatidylglycerol is desirably from about 520 to about 802, preferably from about 688 to about 802 and more preferably from about 744 to about 802. The molecular weight of the poly(ethylene glycol) moiety is desirably from about 851 to about 5802, preferably from about 1019 to about 3775 and more preferably from about 2749 to about 2806. The control of the molecular weight of the phosphatidylcholine and the phosphatidylglycerol is an important feature of Applicants' invention.

Some suitable carrier composition ranges are shown below in tabular form.

| Carrier 1 PC (mole %) | PG (mole %) | PEG-PE (mole %) |
|---|---|---|
| 0-99.4 Preferred | 0-99.4 | 0.5-10 |
| 60-90 Most Preferred | 10-40 | 1-5 |
| 70-80 | 20-30 | 2-5 |

| Carrier 2 PC (mole %) | PG (mole %) | PEG-PE (mole %) | CHOL (mole %) |
|---|---|---|---|
| 0-99.4 Preferred | 0-99.4 | 0.5-10 | 0.5-33 |
| 60-90 Most Preferred | 10-40 | 1-5 | 0.5-20 |
| 70-80 | 20-30 | 2-5 | 0.5-10 |

| Composition 1 PC (mole %) | PG (mole %) | PEG-PE* (mole %) | DRUG (mole %) |
|---|---|---|---|
| 0-98.5 Preferred | 0-98.5 | 0.5-10 | 1-33 |
| 60-90 Most Preferred | 10-40 | 1-5 | 1-33 |
| 70-80 | 20-30 | 2-5 | 1-33 |

*The molecular weight of the PEG is limited to 350.

| Composition 2 PC (mole %) | PG (mole %) | PEG-PE* (mole %) | CHOL (mole %) | DRUG (mole %) |
|---|---|---|---|---|
| 0.1-99.4 Preferred | 0.1-99.4 | 0.5-10 | 0.1-33 | 1-33 |
| 60-90 Most Preferred | 10-40 | 1-5 | 0.1-20 | 1-33 |
| 70-80 | 20-30 | 2-5 | 0.1-10 | 1-33 |

*The molecular weight of the PEG is limited to 350.

Many of the commonly used sterically stabilized liposomes used for intravenous treatments are not suitable for use in the lungs. For instance distearoylphospatidylcholine, which has a high gel-liquid crystalline phase transition temperature of about 54° C., is a commonly used primary phospholipid in sterically stabilized liposomes for intravenous treatment.

The gel-liquid crystalline phase transition temperature of the mixed phospholipids in the sterically stabilized liposome carrier should be in the range from about −20° C. to about 44° C. and preferably from about −10 to about 42° C. It is expected that for sterically stabilized liposome carriers containing cholesterol, the transition range will be broadened compared to that of sterically stabilized liposome carriers containing phospholipids alone. The inclusion of cholesterol will enable a lipid composition with a relatively high transition temperature (e.g., in the gel phase at 37° C.) to have a substantial portion of the membrane in the fluid or liquid crystalline phase at body temperature. This is an important feature of Applicants' invention. The drugs, which can be encapsulated with the sterically stabilized liposome carrier of the present invention, comprise substantially any drug that is useful to treat diseases via the respiratory tract of a mammal. It is anticipated that most drugs that are useful in such treatments will be compatible with the sterically stabilized liposomes. Typically, the carriers and the encapsulated drugs are administered via an aerosol to the respiratory tract.

Both the phosphatidylcholine and the phosphatidylglycerol meeting the criteria set forth in this application can be used alone with poly (ethylene glycol) as the carrier either without or with cholesterol in amounts from about 0.1 to about 33 mole percent. The same drugs are effective (PC and PG with PEG or PC or PG with PEG and with or without cholesterol) in the ranges in the Tables above as long as the criteria in this application are met to insure compatibility with the mammal respiratory tract.

Types of drugs that can be included in the sterically stabilized liposome carriers are not limited so long as the formation and stability of an encapsulation in the sterically stabilized liposome carrier is not adversely affected.

The combined sterically stabilized liposome carriers and drugs are prepared to have unilamellar or multilamellar vesicles of sizes up to about 0.05 to about 5 microns. Preferably the composition is prepared to have substantially homogeneous sizes in a selected size range, with the average diameter typically being up to about 0.02 to about 2.5 micrometers. One method for obtaining the desired size is extrusion of the composition through polycarbonate membranes having pores of a selected size, such as up to about 0.05 to about 5 micrometers.

Some drugs that are effective for treatment of the respiratory tract of a mammal, and are considered particularly suitable are inhaled corticosteroids; such as, budesonide, flunisolide, triamcinolone, beclomethasone, fluticasone, mometasone, dexamethasone, hydrocortisone, methylprednisolone, prednisone, cortisone, betamethasone, or the like. Some other suitable drugs are bronchodilators; such as terbutaline, albuterol, ipatropium, pirbuterol, epinephrine, salmeterol, levalbuterol, formoterol, or the like. Chromolyn sodium and albuterol sulfate are also suitable drugs.

Other drugs that are also considered to be effective and suitably administered using the sterically stabilized liposome carriers of the present invention include, but are not limited to, leukotriene inhibitors; such as montelukast, zafirlukast, zileuton, or the like, as well as antihistamines; such as loratadine, cetirizine or the like. Anti-Tuberculosis drugs for MTB or atypical mycobacteria; such as, isoniazid, ethambutol, pyrazinamide, rifamycin; rifampin, streptomycin, clarithromycin, or the like, are also considered to be suitable. Other drugs; such as the serine lung protease inhibitor (SLPI), azelastine, and theophylline; and other peptides, such as those that relate to Allergy Immunotherapy for indoor and outdoor allergens, or the like, may also be considered suitable. Additionally, amikacin, gentamicin, tobramicin, rifabutin, rifapentine, sparfloxacin, ciprofloxacin, quinolones, azithromycin, erythromycin, or the like, are considered to be suitable. Monophosphoryl lipid A (MPL) is a suitable drug.

Most previously disclosed attempts using liposomes have been with conventional liposomes and only a select few with sterically stabilized liposomes have been used in attempts to extend the effective life of select drugs used in the bloodstream of mammals. These liposomes must exist in a radically different environment than in the respiratory tract of a mammal. Particularly in the lungs, certain surfactant requirements exist for materials which are compatible with the fluids in the lungs and the like as discussed above. Further the conventional liposome carriers delivered to the lungs are susceptible to attack by phagocytic cells as are conventional liposomes used to position drugs in the bloodstream, which are eventually cleared mostly by liver and spleen macrophages. Further most uses of liposomes encapsulating drugs in the bloodstream are administered via intravenous injections. While it is not clear what mechanisms exist that permit sterically stabilized liposomes to exist for longer periods of time in certain portions of the body than would be anticipated for liposomes that were not sterically stabilized, it is clear that the sterically stabilized liposome carriers of the present invention are remarkably stable in the respiratory tract environment and are effective to greatly extend the effective life of encapsulated drugs used to treat various diseases of the respiratory tract.

The preparation of the sterically stabilized liposome carriers, the encapsulation and use of corticosteroid drugs, a peptide (D-4F), a protease inhibitor (SLPI) and monophosphoryl lipid A (MPL) in the carrier, and treatments of mice according to the present invention, are demonstrated in the following examples to show the broad applicability of the carrier.

Methods

Animals

Six week-old male C57 black 6 mice were purchased from Charles River Laboratories, Inc., Wilmington, Mass. The animals were provided with an ovalbumin-free diet and water ad libitum and were housed in an environment-controlled, pathogen-free animal facility. All animal protocols were approved by the Animal Care Committee of the University of Illinois at Chicago, the Medical College of Wisconsin and the Zablocki Veterans Administration Medical Center, and were in agreement with the National Institute of Health's guidelines for the care and use of laboratory animals.

Ovalbumin Sensitization

The animals were sensitized with ovalbumin (OVA). On day 0, each mouse was anesthetized with methoxyflurane given by inhalation. A fragmented heat-coagulated OVA implant was inserted subcutaneously on the dorsal aspect of the cervical region.

For a ten-day period (days 14-24), each mouse was given a 30-minute aerosolization of a 6% OVA solution on alternate days. This method of sensitization led to significant elevations in eosinophil peroxidase (EPO), peripheral blood (PB) eosinophils, and serum IgE levels, along with lung inflammation as seen on histophathology by day 24.

Each of the nebulization doses was given at a volume of 1 milliliter for 2 minutes through use of a chamber in which the mouse was allowed to breathe freely. All treatment groups were compared with either sensitized untreated (SENS) or unsensitized (Normal) mice.

Drugs and Reagents

BUD for daily therapy was diluted from premixed vials (0.25 mg/ml) commercially available from AstraZeneca Pharmaceutical, Wayne, Pa., and was administered via a Salter Aire Plus Compressor, Salter Labs, Irvine, Calif. BUD for encapsulation and N-2-hydroxethylpiperzine-N'-2-ethanesulfonic acid (HEPES) was purchased from Sigma Chemical, St. Louis, Mo. Phosphatidylcholine (PC), phosphatidylglycerol (PG), and poly (ethylene glycol)-distearoylphosphatidylethanolamine (PEG-DSPE) were obtained from Avanti Polar Lipids, Alabaster, Ala. Cholesterol was purchased from Calbiochem, La Jolla, Calif. NaCl and KCl were purchased from Fisher Scientific, Pittsburgh, Pa.

Liposome Preparation

Budesonide (BUD) was encapsulated into either sterically stabilized phosphatidylglycerol [PG]: phosphatidylcholine [PC]: cholesterol: poly(ethylene glycerol)[PEG] distearoylphosphatidylethanolamine [DSPE]-[PG:PC:Cholesterol:PEG-DSPE] (2:8:5:0.5) in the sterically stabilized liposomes or conventional (phosphatidylglycerol-phosphatidylcholine-cholesterol) (2:8:5) as a carrier through use of a modified protocol derived from the protocol described by Gangadharam, et al., Antimicrob Agents Chemother, 1995:39:725-730.

Triamcinolone (TRI) was encapsulated into either sterically stabilized phosphatidylglycerol [PG]: phosphatidylcholine [PC]: cholesterol: poly (ethylene glycerol) [PEG] distearoylphosphatidylethanolamine [DSPE]-[PG: PC: Cholesterol: PEG-DSPE] (2:8:5:0.5) sterically stabilized liposomes.

A portion of the cholesterol used in control liposomes was replaced by BUD or TRI dissolved in chloroform-methanol (2:1) during the preparation of the lipid mixture. The resulting composition was PG: PC: Cholesterol: PEG-DSPE: BUD (2:8:3:0.5:2). Lipids were dried onto the sides of a round-bottomed glass flask or glass tube by rotary evaporation. The dried film was then hydrated by adding sterile 140 mmol/L, NaCl and 10 mmol/L HEPES (pH 7.4) and vortexing.

The resulting multilamellar liposome preparations were extruded 21 times through polycarbonate membranes (either 0.2 or 0.8 μm in pore diameter), (Nuclepore, Pleasanton, Calif.) through use of an Avestin extrusion apparatus, Toronto, Canada. The control carriers were prepared the same way and of the same composition except that no BUD was added. The resulting multilamellar liposome preparation contained about 96.8 weight percent water and was diluted to suitable concentration (20 μg/ml) for administration by nebulization for use.

Liposomes without cholesterol were prepared in a similar manner, except that the molar ratio of the lipids was PG: PC: PEG-DSPE (2:8:0.5).

Liposomes containing MPL were prepared in a similar manner, except that the molar ratio of the lipids was PG:PC: MPL:PEG-DSPE (2:8:0.1:0.5). Liposomes containing both MPL and budesonide were also prepared, in the ratio PG:PC: BUD:MPL:PEG-DSPE (2:8:2:0.1:0.5). Both liposomes were extruded 21 times through polycarbonate membranes with a pore diameter of 0.8 μm.

Liposomes containing SLPI were prepared by first drying the lipids at a molar ratio of PG:PC:PEG-DSPE (2:8:0.5), and then hydrating the lipids in sterile 140 mmol/L, NaCl and 10 mmol/L HEPES (pH 7.4) containing 1 mg/ml SLPI, and proceeding with the extrusion step as above.

Liposomes containing D-4F were prepared by hydrating PG:PC:PEG-DSPE (2:8:0.5) or control PG:PC (2:8) liposomes in Hepes-buffered saline containing the peptide D-4F at a D-4F:lipid molar ratio of 1:40, and then extruding the liposomes 21 times through polycarbonate membranes of 0.2 μm pore diameter.

The amounts of lipid used for the Wk-Empty-S group were based on the amount of lipid nebulized for each of the BUD-encapsulated liposomes (1.39 μmol for the sterically stabilized liposomes and 3.19 μmol for the conventional liposomes).

The dose of BUD chosen was based on preliminary dose-response studies with 5 to 50 μg of BUD as follows.

Each day, 5, 10, 15, 20 or 50 μg of BUD was administered via nebulization to groups of sensitized mice, and the dose-dependent effects on the inflammatory parameters were evaluated. These data were compared with data for either a group of sensitized untreated mice (SENS group) or a group of unsensitized mice (Normal group). A 20 μg/ml dose of BUD was shown on histopathologic examination to effectively decrease EPO activity in bronchoalevolar lavage fluid (BAL), PB eosinophils and inflammation of the lung tissues, along with other inflammatory parameters, without evidence of toxicity to the spleen, liver, bone morrow or gastrointestinal tract. In addition, there were no granulomas or abnormalities in any of the tissues evaluated.

Histopathology Observations

Histopathological examinations performed with and without Methacholine challenge are as follows:

The lungs were removed and fixed with 10% phosphate buffered formalin. Tissue samples were taken from the trachea, bronchi, large and small bronchioles, interstitium, alveoli, and pulmonary blood vessels. The tissues were embedded in paraffin, sectioned at 5 μm thickness and stained with hematoxylin and eosin and analyzed using light microscopy at 100× magnification.

Coded slides were examined by a veterinary pathologist in a blinded fashion for evidence of inflammatory changes, including bronchiolar epithelial hyperplasia and wall thickening, bronchiolar, peribronchiolar and perivascular edema and accumulation of eosinophils, neutrophils, and mononuclear inflammatory cells. Each of the parameters evaluated was given an individual number score. Objective measurements of histopathological changes include number of eosinophils surrounding the bronchi, aggregation of eosinophils around blood vessels (perivascular), accumulation of other inflammatory cells, presence of desquamation and hyperplasia of the airway epithelium, mucus formation in the lumen of the airways and infiltration of inflammatory cells surrounding the alveoli.

Quantitative Histopathology Scoring System

| TRACHEA | BRONCHI | LARGE BRONCHIOLES | SMALL BRONCHIOLES | ALVEOLAR INTERSTITIUM | Alveoli |
|---|---|---|---|---|---|
| Epithelium | Epithelium | Epithelium | Epithelium | Thickening(mm) | Thickening(mm) |
| Hyperplasia(mm) | Hyperplasia(mm) | Hyperplasia(mm) | Hyperplasia(mm) | Edema(mm) | Edema(mm) |
| Desquamation | Desquamation | Desquamation | Desquamation | Cells(#)-PMNs(#), | Cells(#)-PMNs(#), |
| Submucosa | Submucosa | Submucosa | Submucosa | Eosinophils(#) | Eosinophils(#) |
| Edema(mm) | Edema(mm) | Edema(mm) | Edema(mm) | Microgranulomas | Multinucleated- |
| Cells(#)-PMNs(#), | Cells(#)-PMNs(#), | Cells(#)-PMNs(#), | Cells(#)-PMNs(#), | Cells(#)-PMNs(#), | Giant |
| Eosinophils(#) | Eosinophils(#) | Eosinophils(#) | Eosinophils(#) | Eosinophils(#) | Cells(#) |
| Granulomas | Granulomas | Granulomas | Granulomas | Multinucleated-Giant | Blood Vessels |

-continued

| TRACHEA | BRONCHI | LARGE BRONCHIOLES | SMALL BRONCHIOLES | ALVEOLAR INTERSTITIUM | Alveoli |
|---|---|---|---|---|---|
| Blood Vessels Perivascular edema Perivascular cuffing Cells(#)-PMNS(#), Eosinophils(#) | Blood Vessels Perivascular edema Perivascular cuffing Cells(#)-PMNS(#), Eosinophils(#) | Blood Vessels Perivascular edema Perivascular cuffing Cells(#)-PMNS(#), Eosinophils(#) | Blood Vessels Perivascular edema Perivascular cuffing Cells(#)-PMNS(#), Eosinophils(#) | Cells(#) Blood Vessels Perivascular edema Perivascular cuffing Cells(#)-PMNS(#), Eosinophils(#) | Perivascular edema Perivascular cuffing Cells(#)-PMNS(#), Eosinophils(#) |

Each of the parameters evaluated were given an individual number score. The cumulative score was obtained using the individual scores and designated as no inflammation (0), mild inflammation (1-2), moderate inflammation (3-4), and severe inflammation (5-6). (mm=millimeter)

Eosinophil Peroxidase (EPO) Activity in Bronchoalveolar Lavage (BAL) Fluid and Peripheral Blood (PB) Eosinophils EPO activity was measured in the BAL. In some experimental groups EPO activity was obtained with and without Mch challenge. At the time of sacrifice, the trachea was exposed and cannulated with a ball-tipped 24-gauge needle. The lungs were lavaged three times with 1 ml PBS. All washings were pooled and the samples were frozen at −70° C. The samples were later thawed and assayed to determine EPO activity. EPO in the BAL was assessed as follows. A substrate solution consisting of 0.1 mol/L sodium citrate, 0-phenylenediamine, and $H_2O_2$ (3%), pH 4.5 was mixed with BAL supernatants at a ratio of 1:1. The reaction mixture was incubated at 37° C. and the reaction was stopped by the addition of 4 N $H_2SO_4$. Horseradish peroxidase was used as a standard EPO activity (in international units per milliliter) and was measured by spectrophotometric analysis at 490 nm.

The percentages of eosinophils were obtained by counting the number of eosinophils in 100 white blood cells under a high-power field scope (×100) from the PB smears stained with Wright-Giemsa stain.

Total Serum IgE

Ninety-six well flat bottom plates (Fisher Scientific) were coated with 100 μL per well of 2 μg/ml rat antimouse IgE monoclonal antibody (BD, PharMingen, San Diego, Calif.), and incubated overnight at 4° C. Serum was added at a dilution of 1:50 and incubated overnight at 4° C. Purified mouse IgE (k isotype, small b allo-type anti-TNP: BD PharMingen) was used as the standard for total IgE. The samples were incubated for one hour with biotin-conjugated rate antimouse IgE (detection antibody purchased from Southern Biotechnology, Birmingham, Ala.).

15-Lipooxygenase (15-LO) Activity

Measurement of 15-lipooxygenase expression was performed on fresh lung homogenates by Western blot analysis. D-4F is known to bind 15-HETE, thereby decreasing proinflammatory effects of 15-lipooxygenase activity.

Electron Microscopy Studies

Electron Microscopy studies were performed using standard protocols for preparation and reading of the slides Airway Hyperresponsiveness (AHR) TO Methacholine (Mch)-Methods The effectiveness of the Drug and Carrier combination on airway reactivity or airway hyperresponsiveness (AHR) to Methacholine challenge (Mch) was evaluated by assessing Pulmonary Mechanics. These experiments are designed to demonstrate that the sensitivity of the airway that causes excessive coughing or reactivity (AHR) and the like in asthma sufferers are effectively treated by the use of our Drug/Carrier combination comprising of sterically stabilized liposomes. Pulmonary Mechanics were evaluated as follows:

Animals were sensitized using ovalbumin sensitization as described above under the Animals section.

Comparison of C57/B16, A/J, and BALBc Mice

Using our method of ovalbumin-sensitization, C57/B16, A/J, and BALBc mice were compared in their AHR to Mch challenge, since previous studies have demonstrated an interstrain variability in AHR to Mch challenge. There was no significant strain difference in AHR to Mch challenge between the sensitized C57/B16 and A/J or BALBc mice. Therefore, this study was conducted with C57/B16 mice.

AHR to Mch Challenge

Pulmonary resistance measurements were made after four weeks of therapy. As an antigen challenge and to demonstrate sensitization, an aerosolized dose of 6% ovalbumin was given to each animal 24 hours before the evaluation of the pulmonary mechanics.

The animals were anesthetized with an intraperitoneal injection of a solution of ketamine and xylazine (40 mg/kg body weight for each drug). A 20 mg/kg body weight maintenance dose of pentobarbital sodium was given before placement in the body plethysmogragh. The doses were titrated to maintain a steady level of anesthesia without causing significant respiratory depression.

A tracheotomy was performed and a tracheotomy tube was placed in each animal. A saline-filled polyethylene tube with side holes was placed in the esophagus and was connected to a pressure transducer for measurement of pleural pressure. The mice were then placed in a body plethysmograph chamber for measurements of flow, volume, and pressure.

The tracheostomy tube was connected to a tube through the wall of the plethysmograph allowing the animal to breathe room air spontaneously. The esophageal catheter was connected to a pressure transducer. Proper placement of the esophageal catheter was verified using assessments of pressure-volume-flow loops. A screen pneumotachometer and a Valadyne differential pressure transducer were used to measure flow in and out of the plethysmograph.

The frequency response of the plethysmograph-pneumotachometer system determined using the volume oscillator of an Electromechanical Multifunction Pressure Generator available from Millar Instruments, Inc., Houston, Tex., was such that the amplitude decreased by less than 10% to a frequency of 12 Hz. The maximum breathing frequency in the mice studied was 4.3 Hz.

Signals from the pressure transducer and the pneumotachometer were processed using a Grass polygraph (Model 7) recorder. The flow signal was integrated using a Grass polygraph integrator (Model 7P10) to measure corresponding changes in pulmonary volume. Pressure, flow and volume signal outputs were digitized and stored on computer using an analog-to-digital data acquisition system (CO- DAS—available from Dataq Instruments, Inc., Akron, Ohio). The pressure and volume signals were also displayed to verify catheter placement and monitor the animal during the experiment.

The digitalized data were analyzed for dynamic pulmonary compliance, pulmonary resistance, tidal volume, respiratory frequency and minute ventilation from about six to ten consecutive breaths at each recording event. Compliance and resistance were calculated from pleural pressure, airflow, and volume data.

To correct for the resistance of the tracheal cannula, the pressure-flow curve relationship for the cannula alone was measured. It was found to have resistance of 0.3 $cmH_2$) $mol^{-1}s$, which was then subtracted from the total resistance, measured with the animal in place to determine the pulmonary resistance. Mch challenge was performed after baseline measurements were obtained. Mch (Sigma Chemicals, St. Louis, Mo.) was injected intraperitoneally at three-minute intervals in successive cumulative doses of 30, 100, 300, 1,000 and 3,000 µg.

STUDY Groups

Therapy was initiated on day 25, the day after the OVA sensitization was completed. Sensitized animals received nebulized treatments for four weeks. Each study group consisted of 20 mice and was followed for a four-week period. Five animals from each treatment group and from each of the two control groups, sensitized and unsensitized, were euthanized by means of an overdose of methoxyflurane inhaled 24 hours after the first treatments were given and then at weekly intervals for four weeks. At each time point, measurements of EPO in BAL, PB eosinophils, and total serum IgE levels were obtained and histopathologic examination of the lung tissues was performed.

Data Analysis

One-way ANOVA with Tukey-Kramer multiple comparison data analysis was used for Mch responses using SigmaStat Statistical Software (SPSS Science). EPO activity analysis was performed using the Student t test. Over the Study period, there were no significant increases or decreases in inflammation within each group according to weekly measurements for all of the inflammatory parameters being evaluated. Therefore all the weekly measurements are presented as Cumulative data and are presented as mean+/− standard error of the mean (SEM). A p<0.05 was considered to be statistically significant for all of the above statistical comparisons.

Examples

BUD 1: Comparison of BUD in the Carrier with Conventional Liposomes (FIGS. 1-5)

BUD 1: Treatment Groups

| | |
|---|---|
| NORMAL | Unsensitized, Untreated Normal mice |
| SENS | Sensitized, Untreated Asthmatic mice |

-continued

| | |
|---|---|
| Daily BUD | 20 µg of budesonide without Carrier given daily-Standard therapy |
| WK-S-BUD | 20 µg of budesonide in the Carrier without Cholesterol given once a week |
| WK-C-BUD | 20 µg of budesonide encapsulated in Conventional Carrier without Cholesterol given once a week |
| WK-ES | Buffer loaded empty Carrier without Cholesterol or drug given once a week |
| WK-BUD | 20 µg of budesonide without Carrier given once a week |

BUD 1: Results

| | Histo (FIG. 2) | EPO (FIG. 3) | PB Eos (FIG. 4) | IgE levels (FIG. 3) |
|---|---|---|---|---|
| NORMAL | -- | -- | -- | -- |
| SENS | ↑ | ↑ | ↑ | ↑ |
| Daily BUD | ↓ | ↓ | ↓ | ↓ |
| WK-S-BUD | ↓ | ↓ | ↓ | ↓ |
| WK-C-BUD | ∅ | ∅ | ∅ | ∅ |
| WK-ES | ∅ | ∅ | ∅ | ∅ |
| WK-BUD | ∅ | ∅ | ∅ | ∅ |

| Legend | ↑ | ∅ | ↓ | -- |
|---|---|---|---|---|
| | Mod crate-Severe inflammation | No significant reduction in inflammation | Significant reduction in inflammation | No inflammation |

FIG. 1: Histopathology Picture. Representative specimens stained with hematoxylin-eosin are shown of Budesonide (BUD) treatment. a) NORMAL b) SENS c) WK-S-BUD d) Daily BUD e) WK-C-BUD t) WK-BUD. Original magnification ×100. The lung tissues from SENS group had persistent and significant inflammation compared to NORMAL group. There were significant reductions in lung inflammation when one dose of budesonide (BUD) encapsulated in the carrier was given once a week.

SUMMARY for BUD 1 (FIGS. 1-5): In the set of data given for BUD 1, it was demonstrated that one dose of budesonide (BUD) encapsulated in the Carrier given once a week (WK-S-BUD), significantly reduced lung inflammation as shown by the lung histology pictures (FIG. 1) and histopathology scores (FIG. 2) as well as the lung eosinophil peroxidase activity (EPO) (FIG. 3), serum IgE level (FIG. 4), and peripheral blood eosinophil counts (FIG. 5), as effectively as the same dosage of BUD given once a day (Daily BUD) when compared to the Sensitized Untreated Asthmatic group (SENS) and was comparable to the NORMAL group. Weekly treatments with free BUD without Carrier (WK-BUD), BUD encapsulated in Conventional Carrier (WK-C-BUD) and Empty Carrier (WK-ES) did not have comparable effects.

Figure 6:
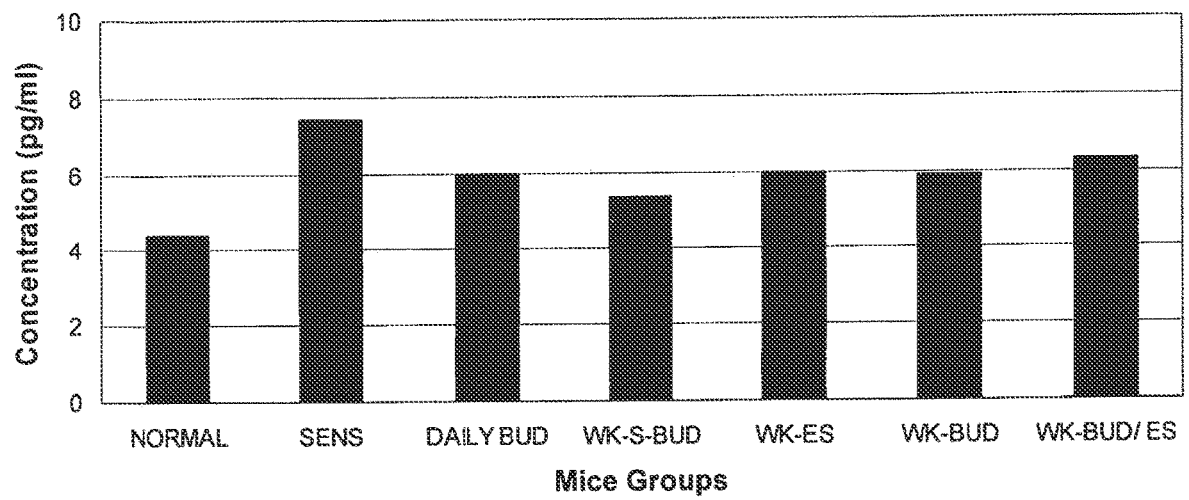
FIGS. 6-8 show graphical presentations of a comparison of the use of BUD encapsulated in the carrier with free BUD and free carrier given simultaneously on lung inflammation for the mice groups tested in BUD 2.
Figure 7:
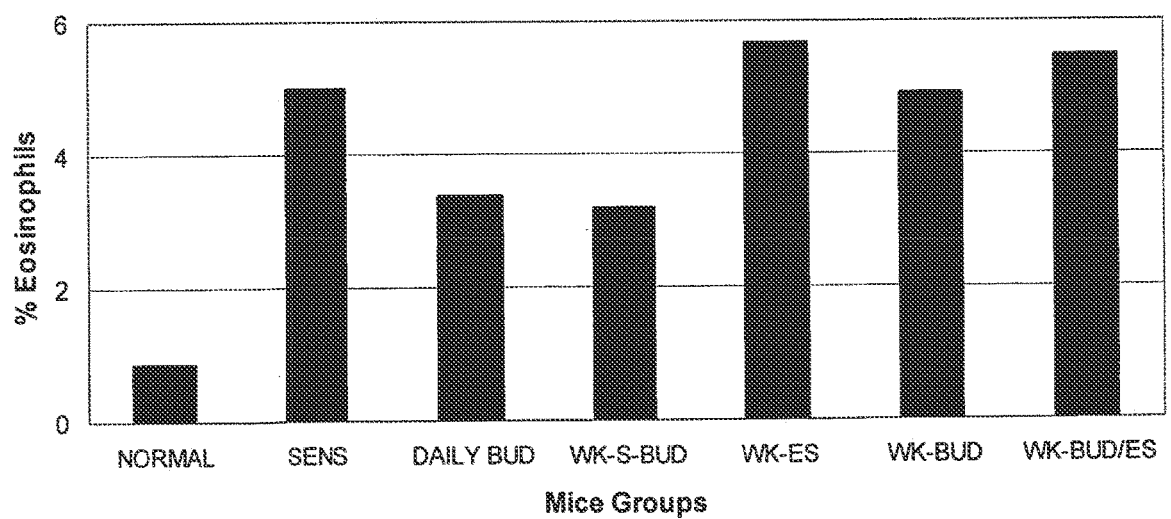
Figure 8:
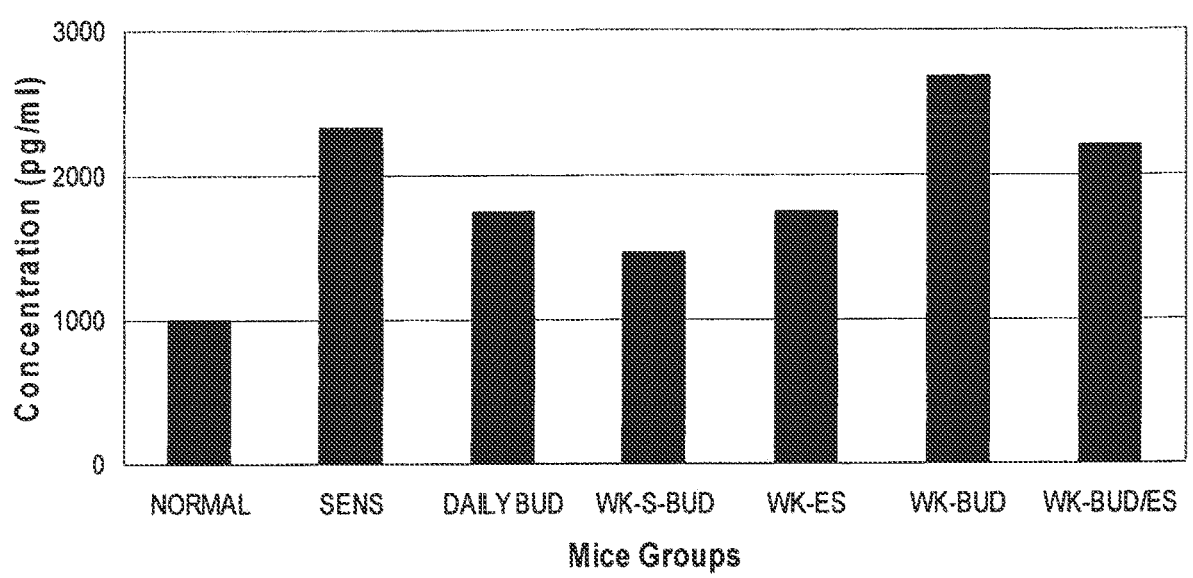

BUD 2: Comparison of BUD in the Carrier with Free Drug/Free Carrier without Encapsulation Given Simultaneously (FIGS. 6-8).

BUD 2: Treatment Groups

| | |
|---|---|
| NORMAL | Unsensitized, Untreated Normal mice |
| SENS | Sensitized, Untreated Asthmatic mice |
| Daily BUD | 20 µg of budesonide without the Carrier given daily-Standard therapy |

-continued

| | |
|---|---|
| WK-S-BUD | 20 μg of budesonide in the Carrier without Cholesterol given once a week |
| WK-ES | Buffer loaded Empty Carrier without Cholesterol or drug given once a week |
| WK-BUD | 20 μg of budesonide without the Carrier given once a week |
| WK-BUD & ES | WK-ES and WK-BUD without encapsulation in the Carrier, given once a week |

BUD 2: Results

| | EPO (FIG. 6) | PB Eos (FIG. 7) | IgE levels (FIG. 8) |
|---|---|---|---|
| NORMAL | -- | -- | -- |
| SENS | ↑ | ↑ | ↑ |
| Daily BUD | ↓ | ↓ | ↓ |
| WK-S-BUD | ↓ | ↓ | ↓ |
| WK-ES | Ø | Ø | Ø |
| WK-BUD | Ø | Ø | Ø |
| WK-BUD & ES | Ø | Ø | Ø |

| Legend | ↑ | Ø | ↓ | -- |
|---|---|---|---|---|
| | Moderate-Severe inflammation | No significant reduction in inflammation | Significant reduction in inflammation | No inflammation |

SUMMARY for BUD 2: In the set of data given for BUD 2, it was demonstrated that one dose of budesonide (BUD) encapsulated in the Carrier given once a week (WK-S-BUD), reduced lung inflammation, lung eosinophil peroxidase activity (EPO) (FIG. 6), serum IgE levels (FIG. 8), and peripheral blood eosinophil (FIG. 7) counts, as effectively as the same dosage of BUD given once a day (Daily BUD) when compared to the Sensitized Untreated Asthmatic group (SENS) and was comparable to the NORMAL group. Weekly treatments with only free BUD without Carrier (WK-BUD), Empty Carrier (WK-ES), or free BUD (WK-BUD) and Empty Carrier (WK-ES) given simultaneously did not have comparable effects.

BUD 3: Comparison of BUD Encapsulated in the Carrier with and without Cholesterol (FIGS. 9-15).

BUD 3: Treatment Groups

| | |
|---|---|
| NORMAL | Unsensitized, Untreated Normal mice |
| SENS | Sensitized, Untreated Asthmatic mice |
| Daily BUD | 20 μg of budesonide without the Carrier given daily-Standard therapy |
| WK-S-BUD+ (plus Chol) | 20 μg of budesonide in the Carrier with Cholesterol given once a week |
| WK-S-BUD-- (minus Chol) | 20 μg of budesonide in the Carrier without Cholesterol given once a week |
| WK-ES-- | Buffer loaded empty carrier without Cholesterol or drug given once a week |
| WK-BUD | 20 μg of budesonide without the Carrier given once a week |

BUD 3: Results

Figures 9E, 9F, 9G, 9H:
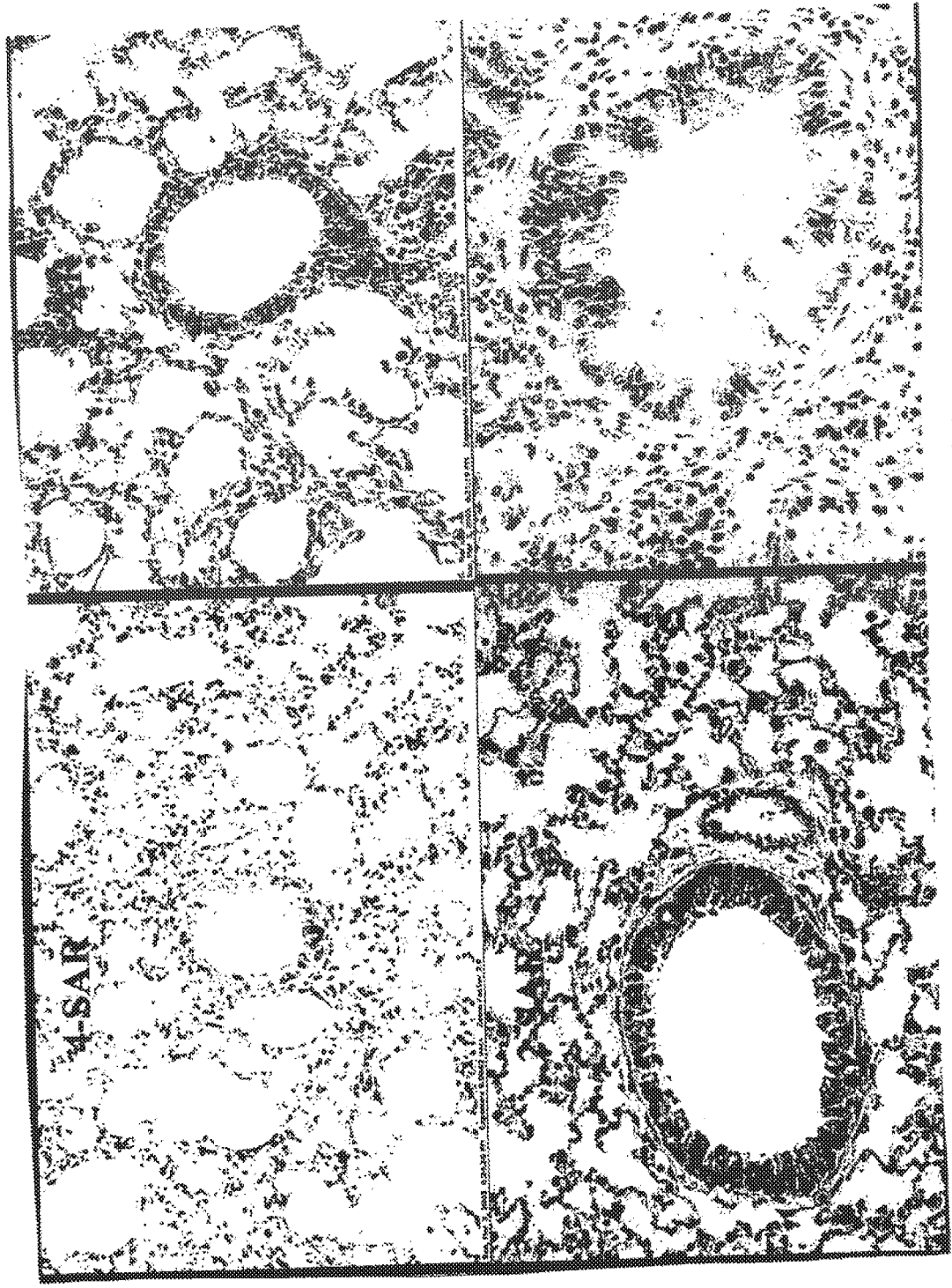

FIG. 9(A-L): Histopathology of the airway hyperreactivity (AHR) responses without (SAR) and with (AR) Methacholine (Mch) challenge with Budesonide (BUD) treatment. Representative specimens are stained with hematoxylin-eosin are shown at a magnification of 100×. a) Normal-SAR b) Normal-AR c) SENS-SAR d) SENS-AR e) WK-S-BUD-SAR WK-S-BUD-AR g) Daily BUD-SAR h) Daily BUD-AR i) WK-BUD-SAR j) WK-BUD-AR k) WK-ES-SAR 1) WK-ES-AR. Original magnification ×100. The lung tissues from SENS group had persistent and significant inflammation compared to NORMAL group with and with Mch challenge. There were significant decreases in lung inflammation only in the WK-S-BUD with and without Mch challenge. Only with the WK-S-BUD and the Normal groups the lung inflammation did not increase significantly with the Mch challenge. There was a significant increase in lung inflammation with Mch challenge with all the other groups including the Daily BUD group.

Figure 2:
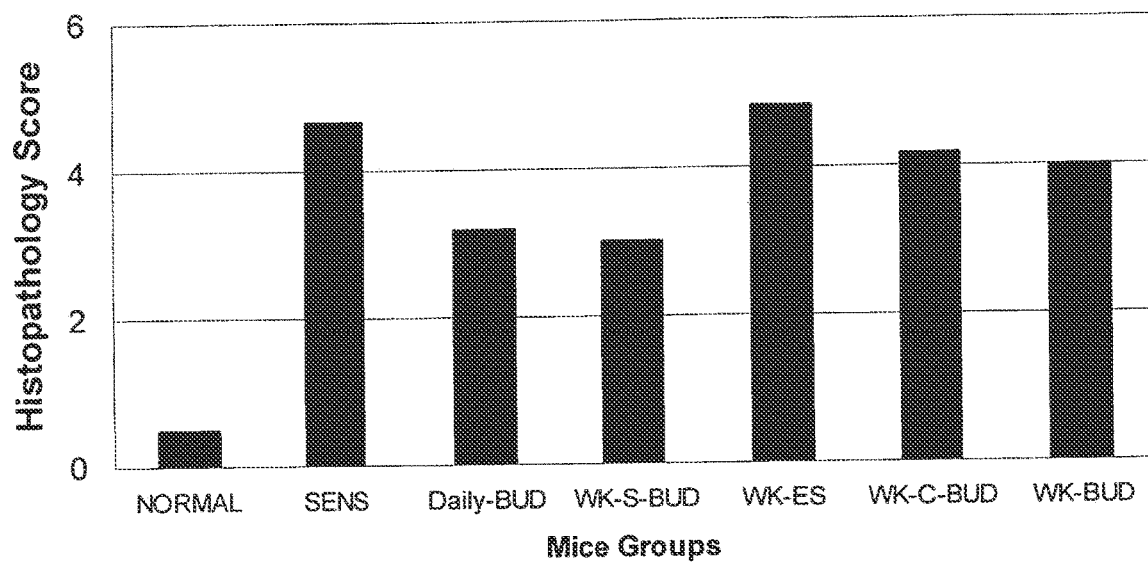
Figure 3:
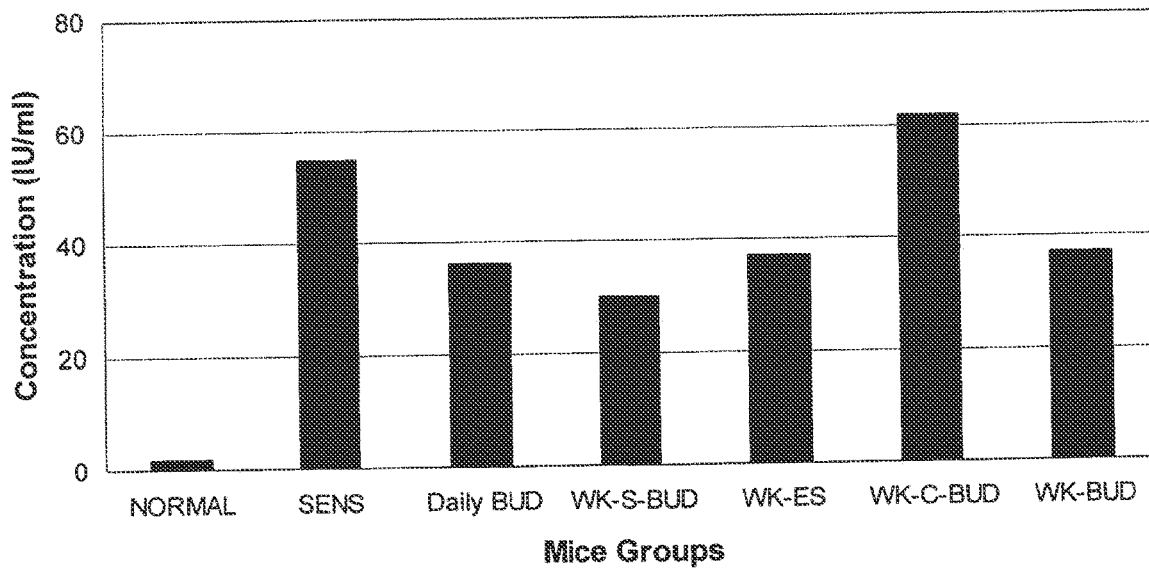
Figure 4:
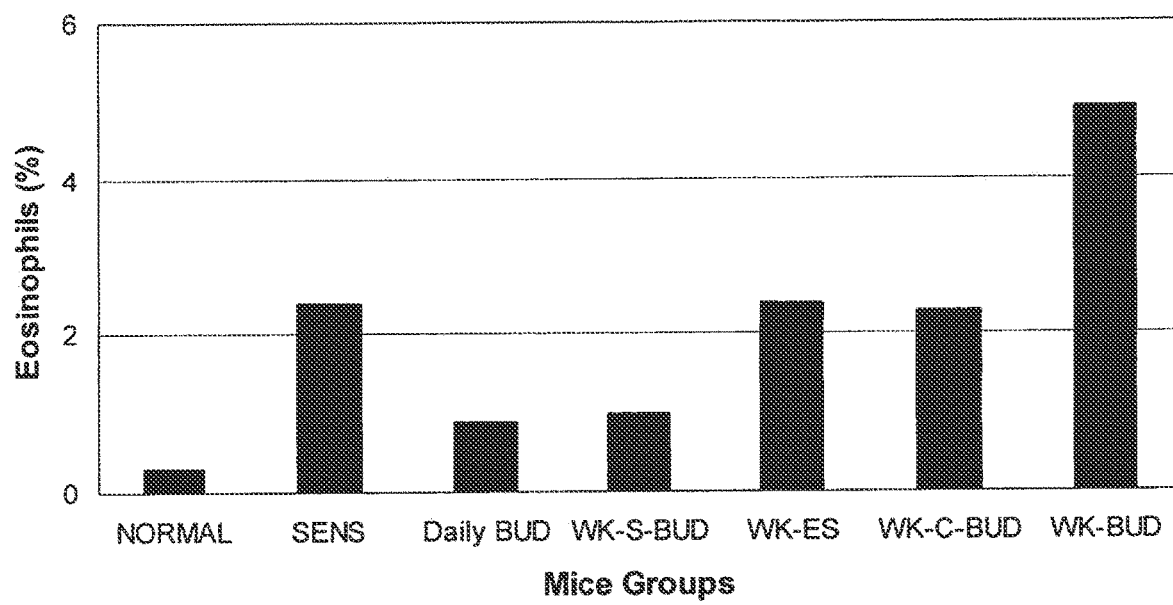
Figure 5:
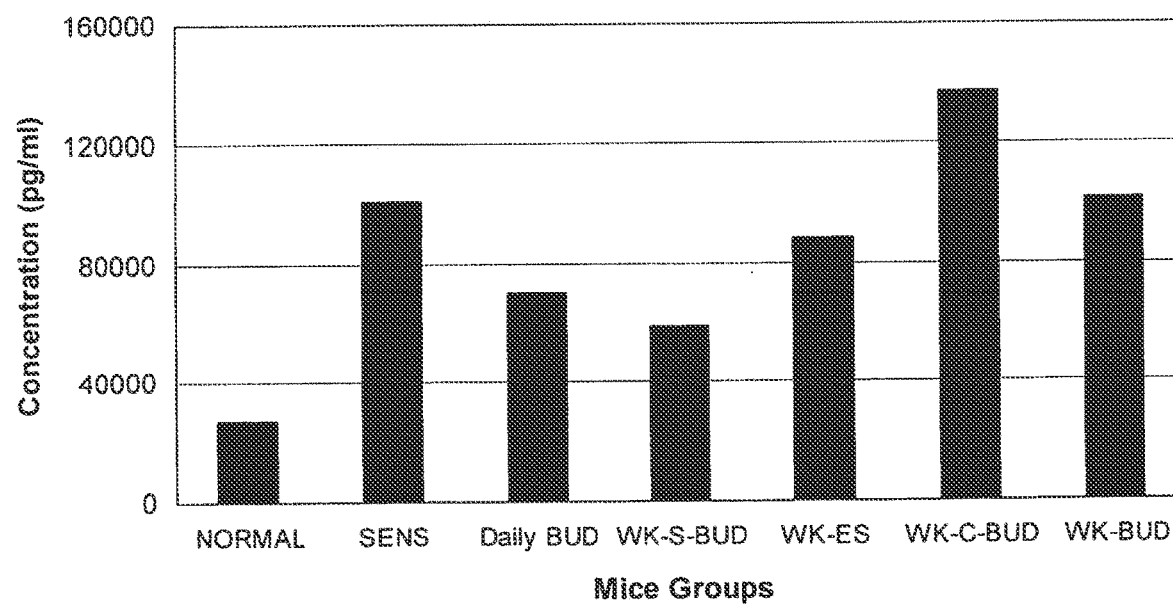
Figure 10:
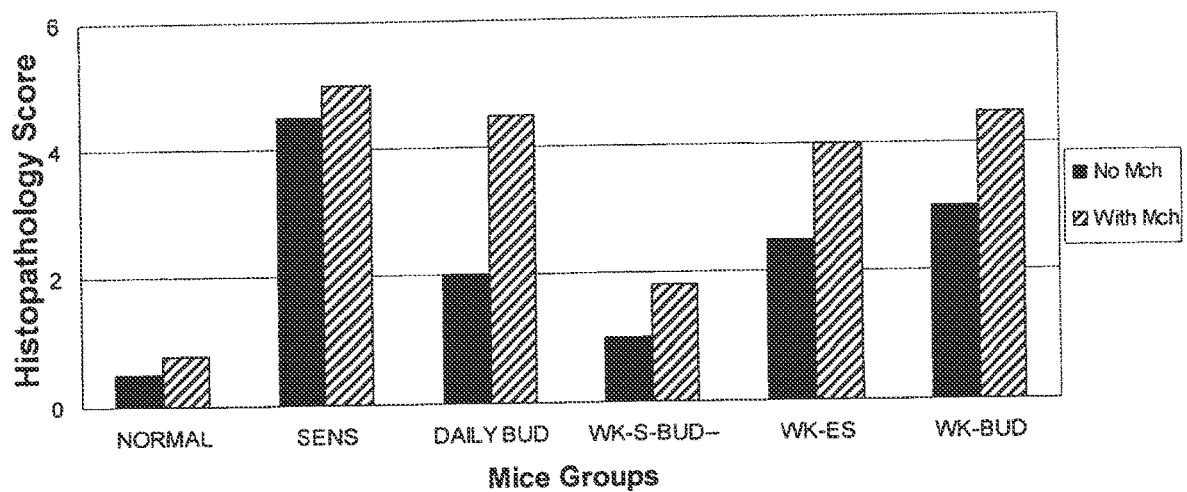
Figure 11:
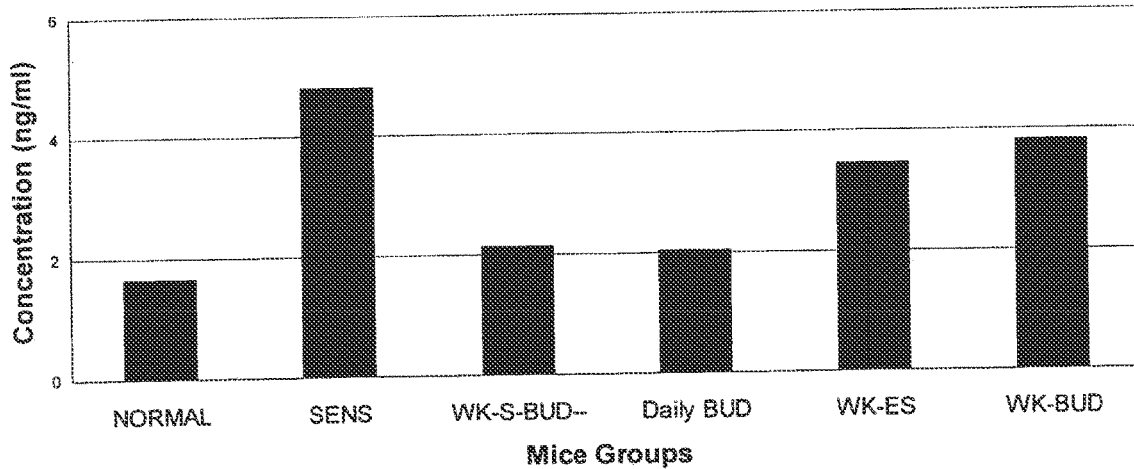
Figure 12:
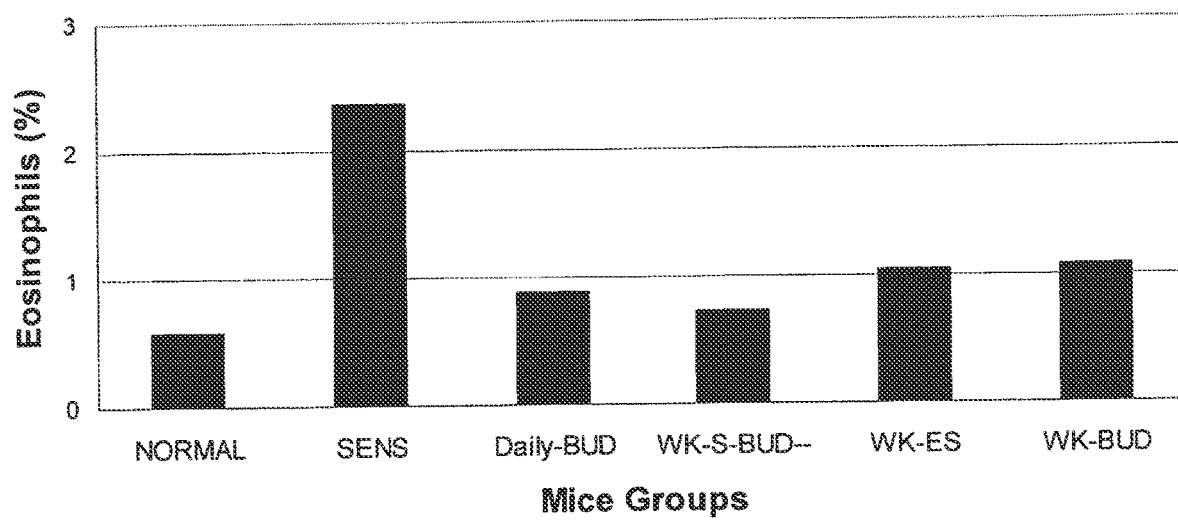
Figure 13:
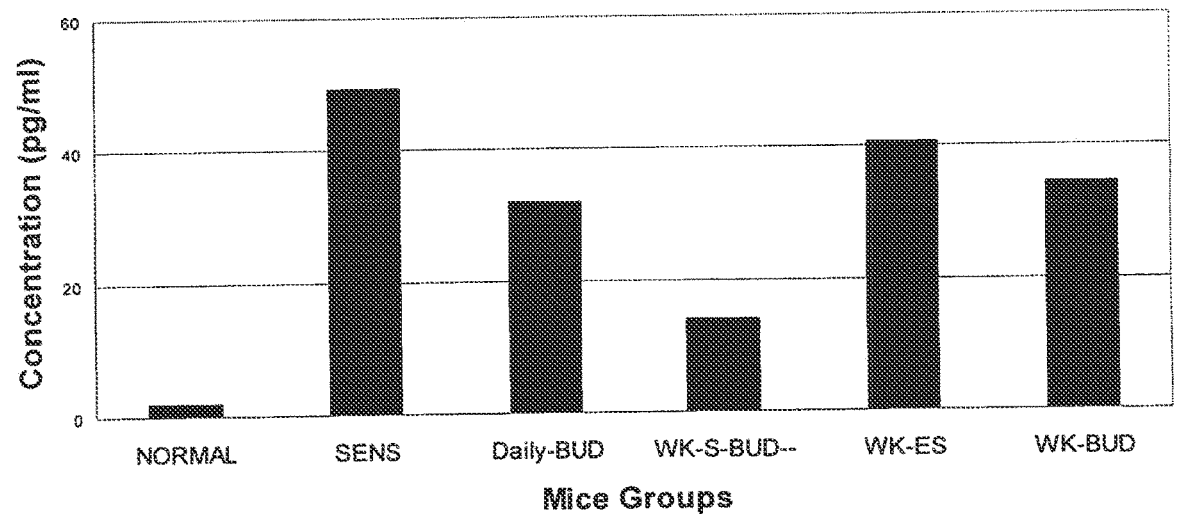
Figure 14:
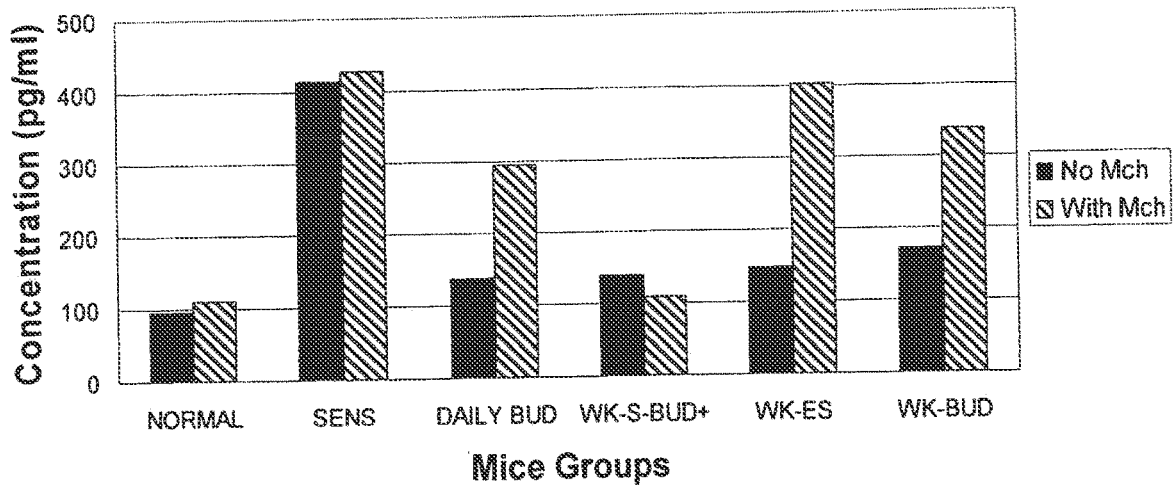
Figure 15:
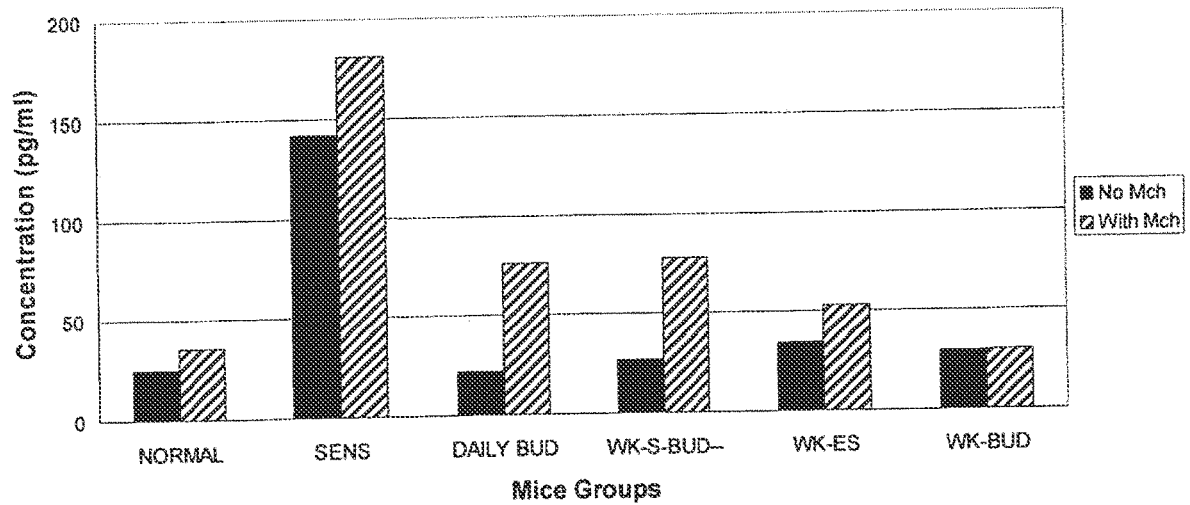

| | Histo Chol (+) FIG. 2 Chol (--) FIG. 10 | EPO Chol (+) FIGS.-3, 6 Chol (--) FIG. 11 | PB Eos Chol (+) FIGS.-4, 7 Chol (--) FIG. 12 | IgE levels Chol (+) FIGS. 5, 8 Chol (--) FIG. 13 |
|---|---|---|---|---|
| NORMAL | -- | -- | -- | -- |
| SENS | ↑ | ↑ | ↑ | ↑ |
| Daily BUD | ↓ | ↓ | ↓ | ↓ |
| WK-S-BUD+ | ↓ | ↓ | ↓ | ↓ |
| WK-S-BUD-- | ↓ | ↓ | ↓ | ↓ |
| WK-ES-- | Ø | Ø | Ø | Ø |
| WK-BUD | Ø | Ø | Ø | Ø |

| | EPO Chol (+) NO Mch (FIG. 14) | EPO Chol (+) With Mch (FIG. 14) |
|---|---|---|
| NORMAL | -- | -- |
| SENS | ↑ | ↑ |
| Daily BUD | ↓ | Ø |
| WK-S-BUD+ | ↓ | ↓ |
| WK-ES-- | Ø | Ø |
| WK-BUD | Ø | Ø |

| | Histo Chol (--) NO Mch (FIG. 10) | Histo Chol (--) With Mch (FIG. 10) | EPO Chol (--) NO Mch (FIG. 15) | EPO Chol (--) With Mch (FIG. 15) |
|---|---|---|---|---|
| NORMAL | -- | -- | -- | -- |
| SENS | ↑ | ↑ | ↑ | ↑ |
| Daily BUD | ↓ | Ø | ↓ | Ø |
| WK-S-BUD-- | ↓ | ↓ | ↓ | ↓ |
| WK-ES-- | Ø | Ø | Ø | Ø |
| WK-BUD | Ø | Ø | Ø | Ø |

| Legend | ↑ | ∅ | ↓ | -- |
|---|---|---|---|---|
| | Moderate-Severe inflammation or AHR | No significant reduction in inflammation or AHR | Significant reduction in inflammation or AHR | No inflammation or AHR |

SUMMARY for BUD 3: In the set of data given for BUD 3, it was demonstrated that BUD encapsulated in the Carrier with (WK-S-BUD+) or without Cholesterol (WK-S-BUD−) given once a week, reduced lung inflammation, lung eosinophil peroxidase activity (EPO), serum IgE levels, and peripheral blood eosinophil counts, and airway hyperreactivity (AHR) to methacholine (MCH) challenge as effectively as the same dosage of BUD given once a day (Daily BUD), when compared to the Sensitized Untreated Asthmatic group (SENS) and, was comparable to the NORMAL group. Only the WK-S-BUD+ and WK-S-BUD− treated groups significantly reduced the Eosinophil Peroxidase Activity and AHR with MCH challenge. BUD in the Carrier without Cholesterol (WK-S-Bud−) was equally effective as BUD encapsulated in the Carrier with Cholesterol (WK-S-BUD+). Weekly treatments with only free BUD without Carrier (WK-BUD) and Empty Carrier without cholesterol (WK-ES−) did not have comparable effects on lung inflammation or AHR as the WK-S-BUD+ and WK-S-BUD− treated groups.

Figure 16:
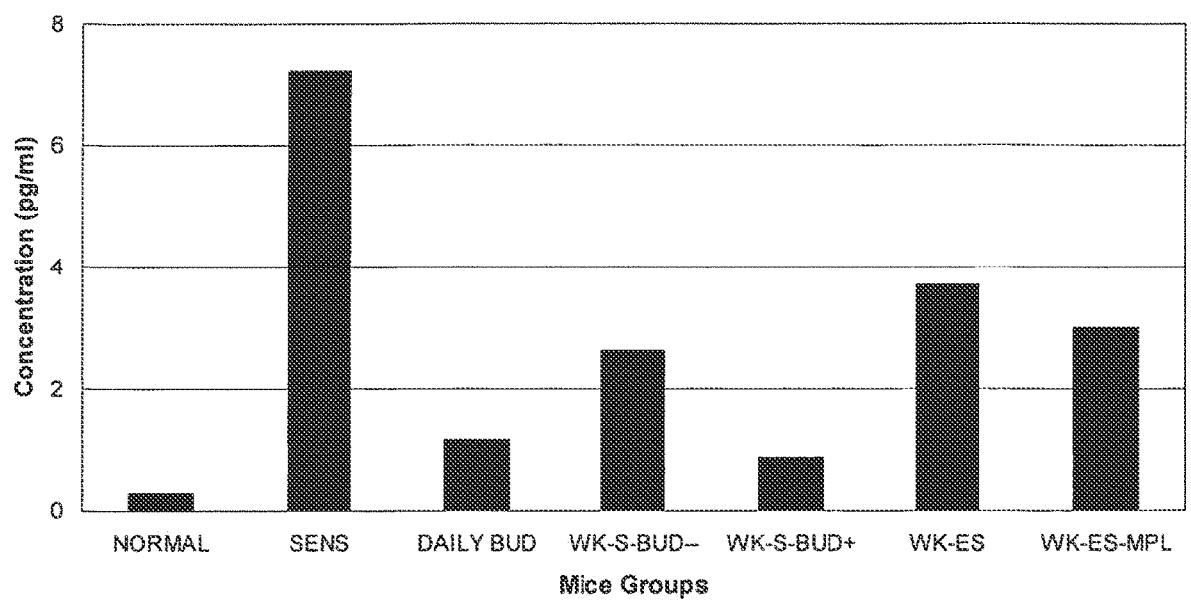
FIGS. 16-18 show graphical presentations of a comparison of the use of BUD encapsulated in the carrier with and without MIT on lung inflammation and AIR and for the mice groups tested in BUD 4.
Figure 17:
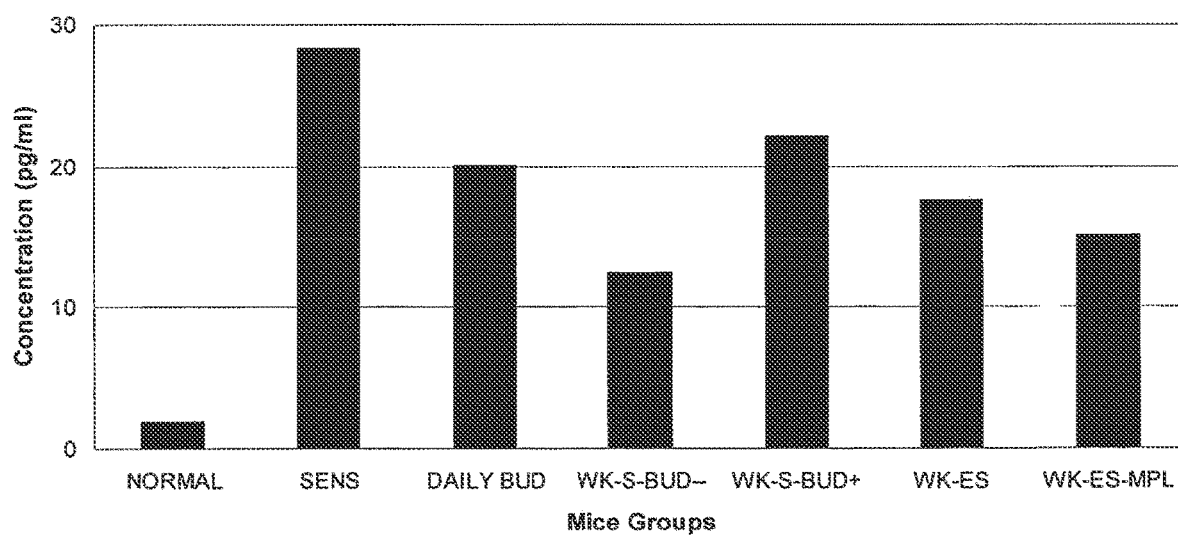
Figure 18:
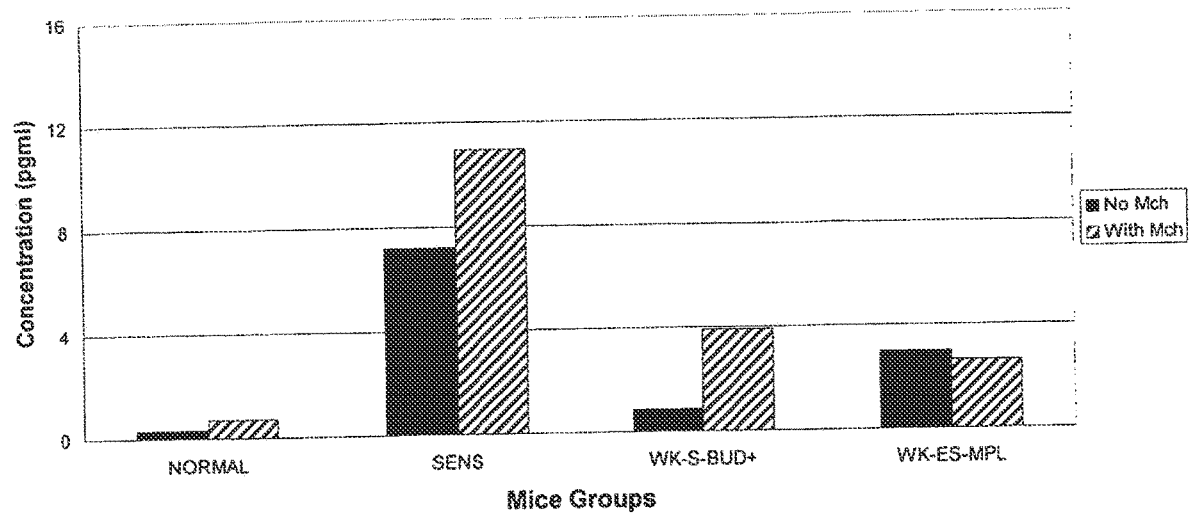

BUD 4: Comparison of BUD in the Carrier with and without MPL (FIGS. 16-18).

BUD 4: Treatment Groups

| | |
|---|---|
| NORMAL | Unsensitized, Untreated Normal mice |
| SENS | Senstized, Untreated Asthmatic mice |
| Daily BUD | 20 µg of budesonide without the Carrier given daily-Standard therapy |
| WK-S-BUD-- (minus MPL) | 20 µg of budesonide in the Carrier without MPL or Cholesterol given once a week |
| WK-S-BUD+ (plus MPL) | 2 µg of budesonide in the Carrier with MPL, without Cholesterol given once a week |
| WK-ES-- | Buffer loaded empty Carrier without MPL, drug, or Cholesterol given once a week |
| WK-ES-MPL | Buffer loaded empty Carrier without drug or Cholesterol, with MPL given once a week |

BUD 4: Results

| | EPO (FIG. 16) | IgE levels (FIG. 17) |
|---|---|---|
| NORMAL | -- | -- |
| SENS | ↑ | ↑ |
| Daily BUD | ↓ | ↓ |
| WK-S-BUD+ | ↓ | ↓ |
| WK-S-BUD-- | ↓ | ↓ |
| WK-ES-- | ∅ | ∅ |
| WK-ES-MPL | ∅ | ∅ |

| | EPO (No Mch) (FIG. 18) | EPO (With Mch) (FIG. 18) |
|---|---|---|
| NORMAL | -- | -- |
| SENS | ↑ | ↑ |
| WK-S-BUD+ | ↓ | ↓ |
| WK-ES-MPL | ↓ | ↓ |

| Legend | ↑ | ∅ | ↓ | -- |
|---|---|---|---|---|
| | Moderate-Severe inflammation or AHR | No significant reduction in inflammation or AHR | Significant reduction in inflammation or AHR | No inflammation or AHR |

SUMMARY for BUD 4: In the set of data given for BUD 4, it was demonstrated that BUD encapsulated in the Carrier with (WK-S-BUD+) or without MPL (WK-S-BUD−) given once a week, reduced lung inflammation, lung eosinophil peroxidase activity (EPO), serum IgE levels, and peripheral blood eosinophil counts, and airway hyperreactivity (AHR) to methacholine (Mch) challenge as effectively as the same dosage of BUD given once a day (Daily BUD) when compared to the Sensitized Untreated Asthmatic group (SENS) and was comparable to the NORMAL group. Only the WK-S-BUD+, WK-S-BUD−, and the weekly Empty Carrier with MPL (WK-ES-MPL) treatment groups significantly reduced the Eosinophil Peroxidase Activity and AHR with Mch challenge. BUD in the Carrier with MPL (WK-S-Bud+) was equally as effective as BUD encapsulated in the Carrier without MPL (WK-S-BUD−). Weekly treatments with Empty Carrier without MPL (WK-ES−) did not have comparable effects on lung inflammation or AHR as the WK-S-BUD+, WK-S-BUD−, or Empty Carrier with MPL (WK-ES-MPL) treated groups.

BUD 5: Comparison of BUD with TRI in the Carrier (FIGS. 19-23).

BUD 5: Treatment Groups

| | |
|---|---|
| NORMAL | Unsensitized, Untreated Normal mice |
| SENS | Senstized, Untreated Asthmatic mice |
| Daily BUD | 20 µg of budesonide without the Carrier given daily-Standard therapy |
| WK-S-BUD | 20 µg of budesonide in the Carrier with Cholesterol given once a week |
| WK-S-TRI-20 µg | 20 µg of triamcinolone in the Carrier with Cholesterol given once a week |
| WK-S-TRI-40 µg | 40 µg of triamcinolone in the Carrier with Cholesterol given once a week |
| WK-ES | Buffer loaded empty Carrier without drug or Cholesterol given once a week |

BUD 5: Results

Figure 19:
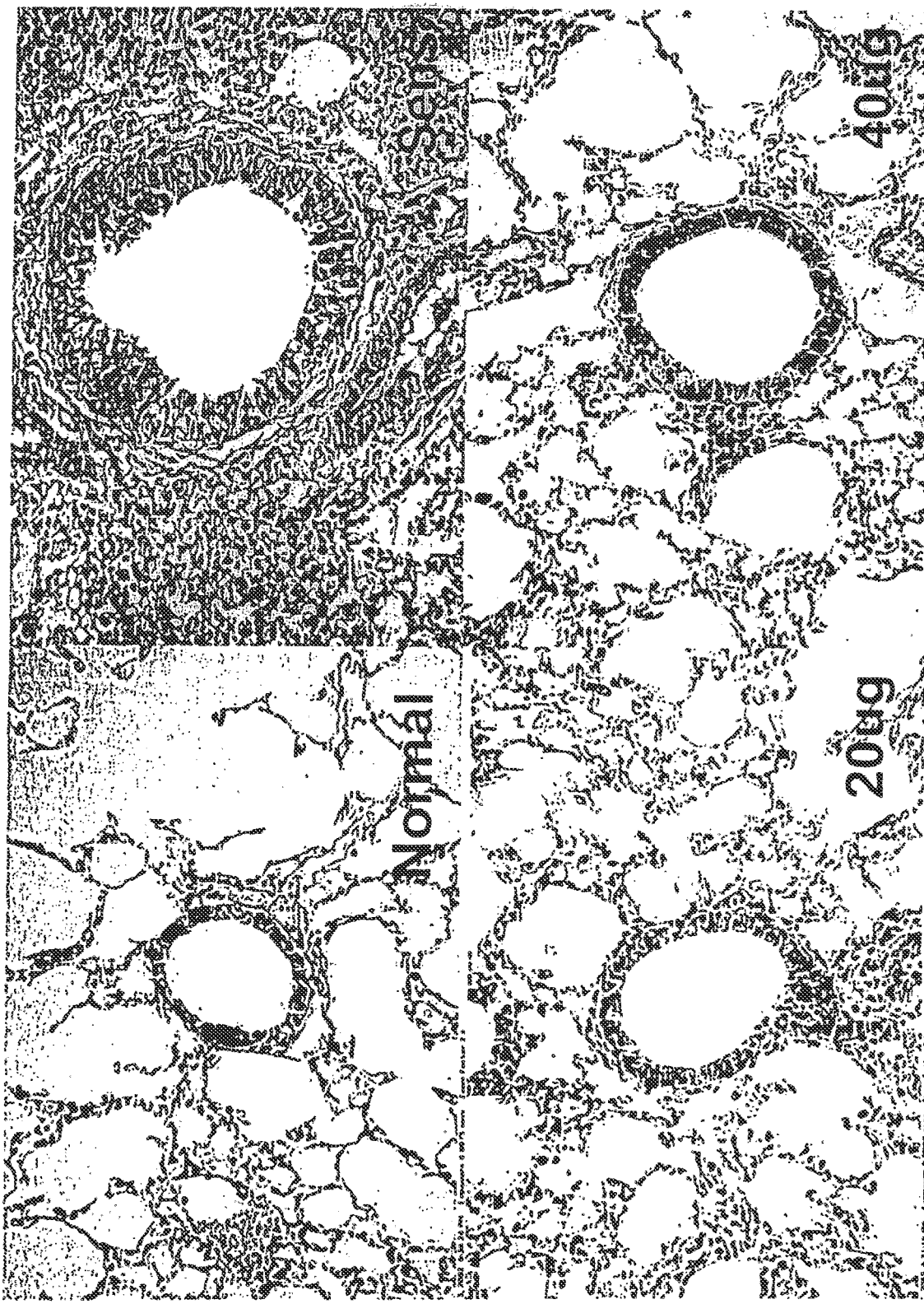
FIGS. 19-23 show graphical and pictorial presentations of a comparison of the use of either BUD or TRI encapsulated in the carrier on lung inflammation and AHR for the mice groups tested in BUD 5.
Figure 20:
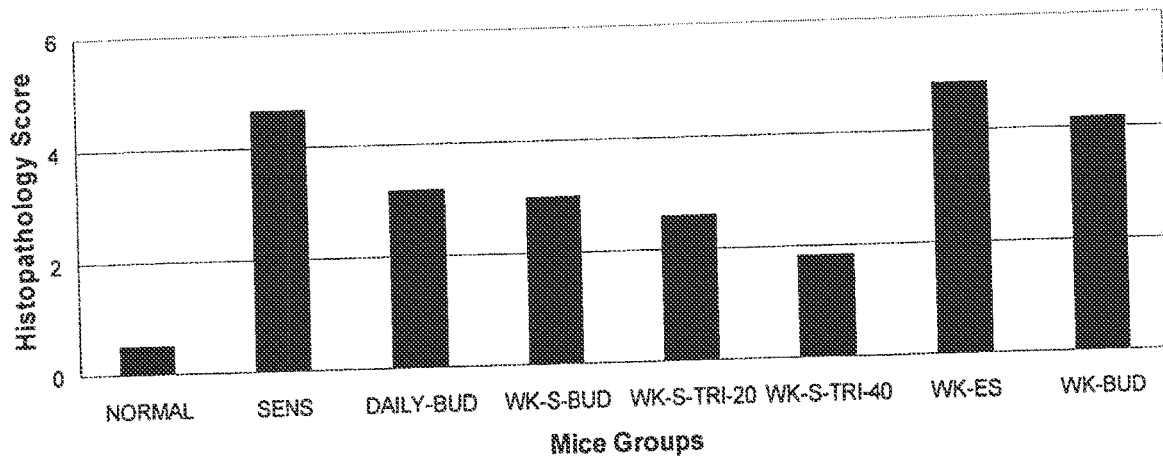
Figure 21:
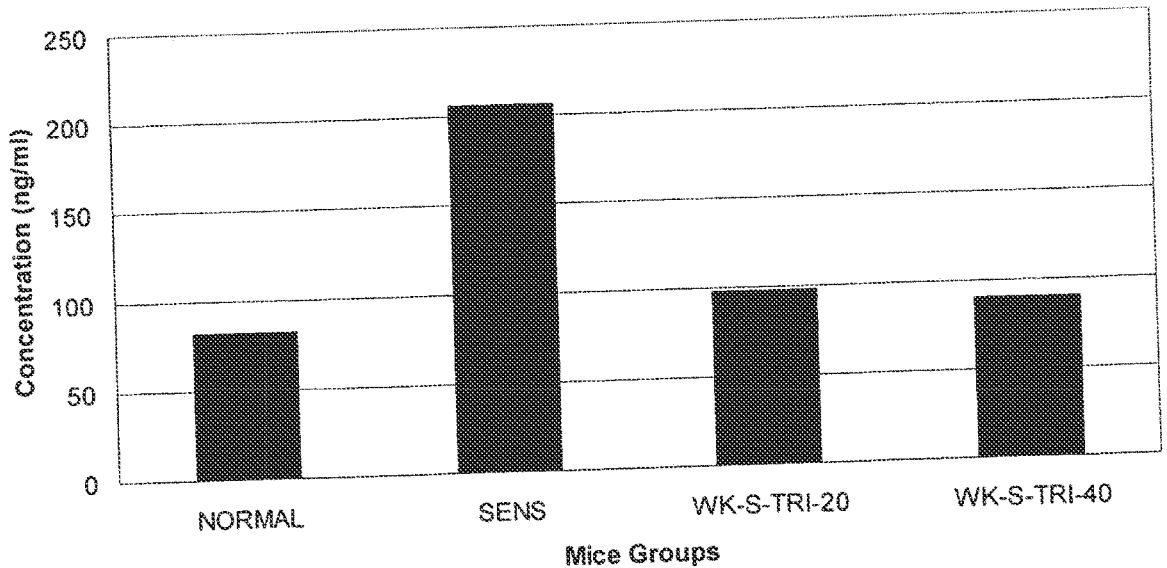
Figure 22:
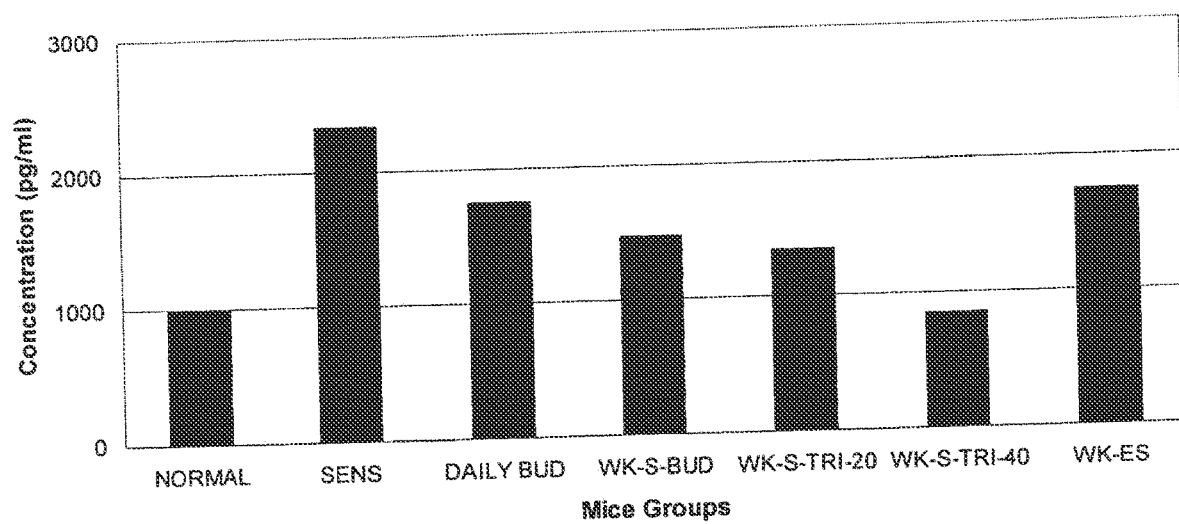
Figure 23:
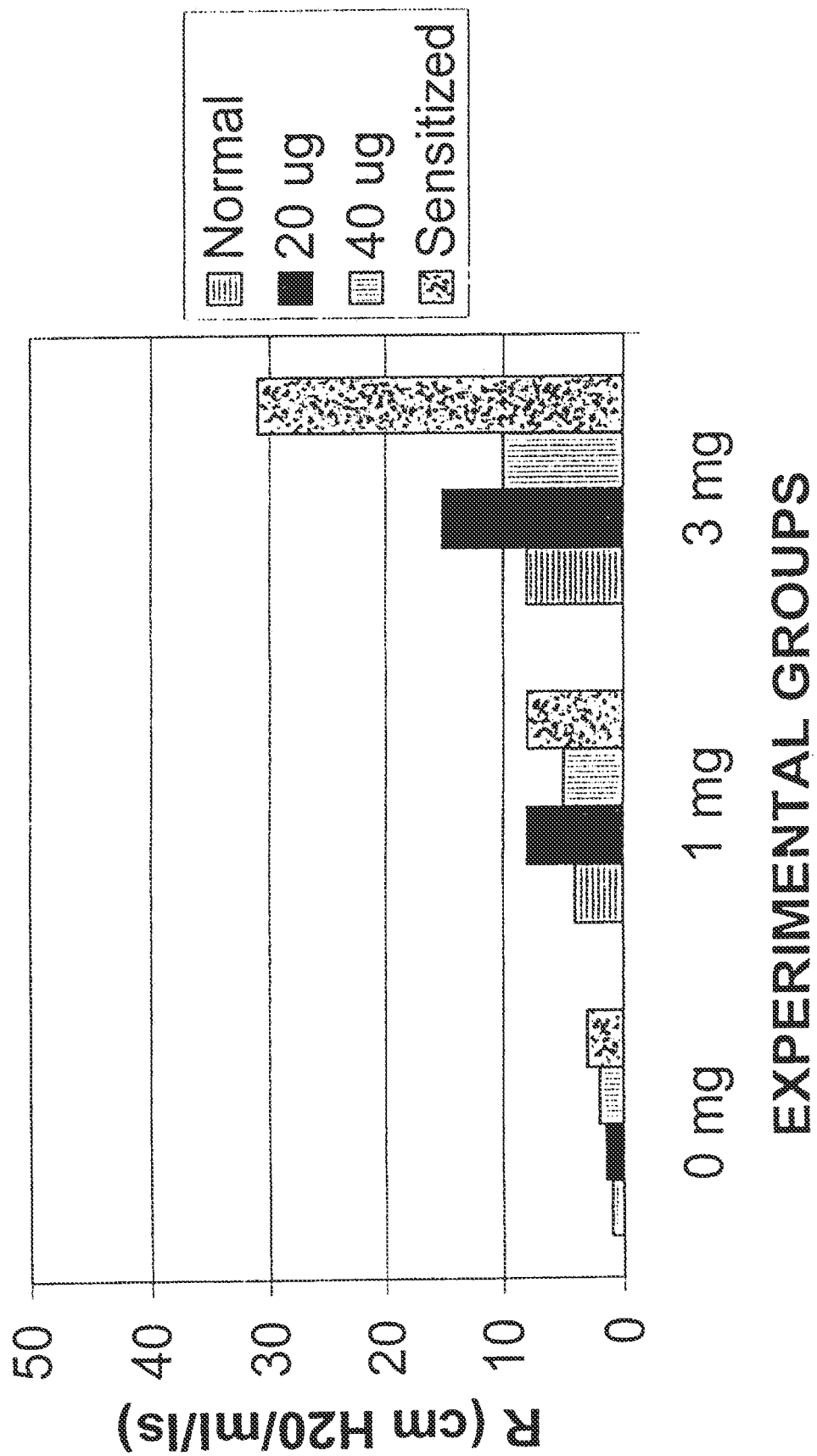

FIG. 19: Histopathology Pictures of treatment with triamcinolone (TRI). Representative specimens stained with hematoxylin-eosin are shown. a) NORMAL b) SENS c) WK-S-TRI-20 µg d) WK-S-TRI-40 µg. Original magnification ×100. The lung tissues from SENS group had persistent and significant inflammation compared to NORMAL group. There were significant decreases in lung inflammation in both the WK-S-TRI-20 µg and WK-S-TRI-40 µg groups when compared to the SENS group.

|  | Histo (FIG. 20) | EPO (FIG. 21) | IgE levels (FIG. 22) | AHR With Mch (FIG. 23) |
|---|---|---|---|---|
| NORMAL | -- | -- | -- | -- |
| SENS | ↑ | ↑ | ↑ | ↑ |
| Daily BUD | ↓ | *N/A | ↓ | *N/A |
| WK-S-BUD | ↓ | *N/A | ↓ | *N/A |
| WK-S-TRI-20 µg | ↓ | ↓ | ↓ | Ø |
| WK-S-TRI-40 µg | ↓ | ↓ | ↓ | ↓ |
| WK-ES | Ø | *N/A | Ø | Ø |

*N/A = Data not available

| Legend | ↑ | Ø | ↓ | -- |
|---|---|---|---|---|
|  | Moderate-Severe inflammation | No significant reduction in inflammation or AHR | Significant reduction in inflammation or AHR | No inflammation or AHR |

SUMMARY: In the set of data given for BUD 5, it was demonstrated that 20 µg of Triamcinolone (TRI) encapsulated in the Carrier (WK-S-TRI-20 µg) or 40 µg of TRI encapsulated in the Carrier (WK-S-TRI-40 µg) given once a week, reduced lung inflammation and airway hyperreactivity (AHR) to methacholine (Mch) challenge as effectively as 20 µg of Budesonide (BUD) encapsulated in the Carrier with (WK-S-BUD) or BUD given once a day (Daily BUD) when compared to the Sensitized Untreated Asthmatic group (SENS) and was comparable to the NORMAL group. WK-S-TRI-20 WK-S-TRI-40 µg, WK-S-BUD, and Daily BUD all reduced the lung inflammation. Only the WK-S-TRI-40 µg and WK-S-BUD significantly reduced the Eosinophil Peroxidase Activity and airway hyperreactivity (AHR) with Mch challenge. The WK-S-TRI-20 µg reduced the AHR to Mch challenge but was not statistically significant. Weekly treatments with Empty Carrier (WK-ES) did not have comparable effects on lung inflammation or AHR to Mch challenge.

D-4F: Effect of D-4F Encapsulated in the Carrier on Lung Inflammation and AHR (FIGS. 24-32)

D-4F: Treatment Groups

| NORMAL | Unsensitized, Untreated Normal mice |
|---|---|
| SENS | Senstitized, Untreated Asthmatic mice |
| Daily D-4F | 20 µg of D-4F without the Carrier given daily, intranasally |
| WK-S-D-4F | 20 µg of D-4F in the Carrier without Cholesterol given intranasally once a week |

D-4F: Results

Figure 24:
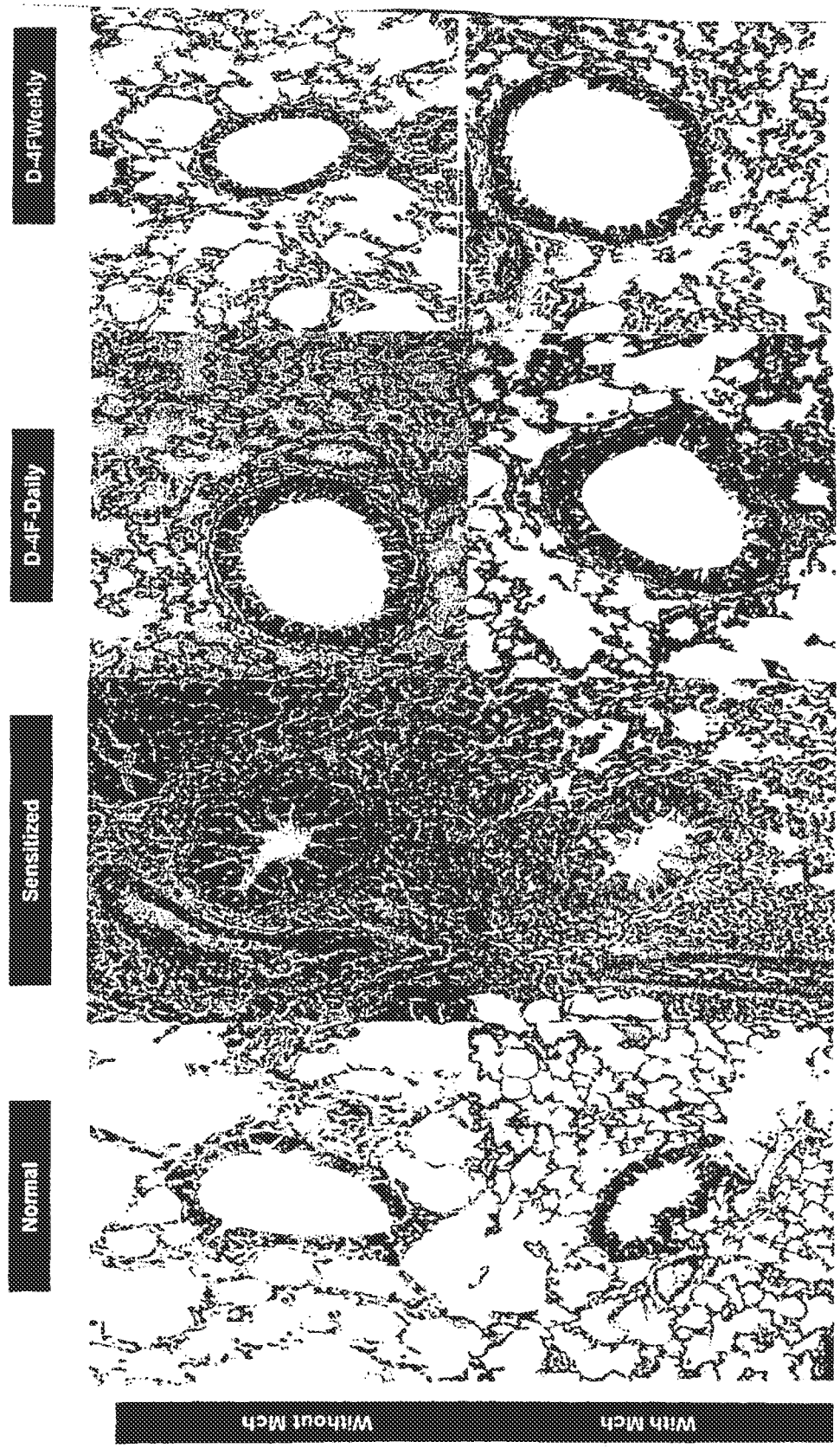
FIGS. 24-32 show graphical and pictorial presentations of the use of D-4F encapsulated in the carrier on lung inflammation and AHR for the mice groups tested in D-4F.
Figure 25:
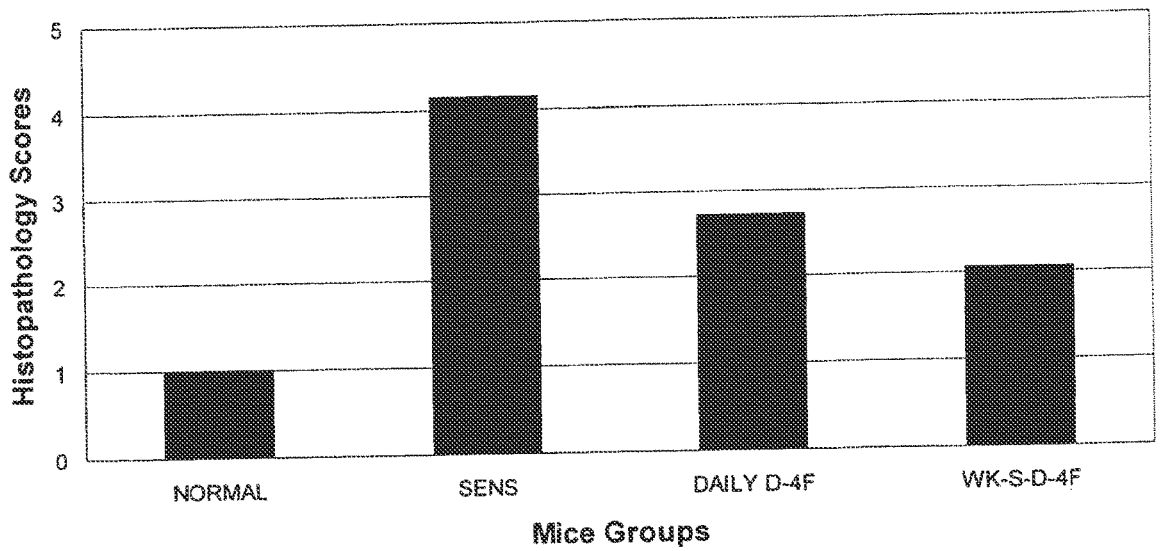
Figure 26:
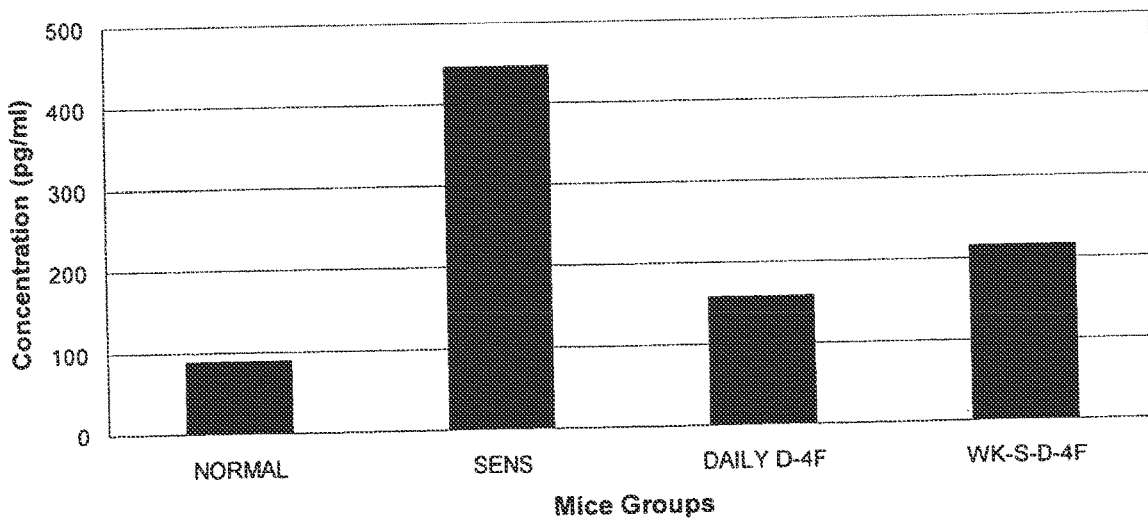
Figure 27:
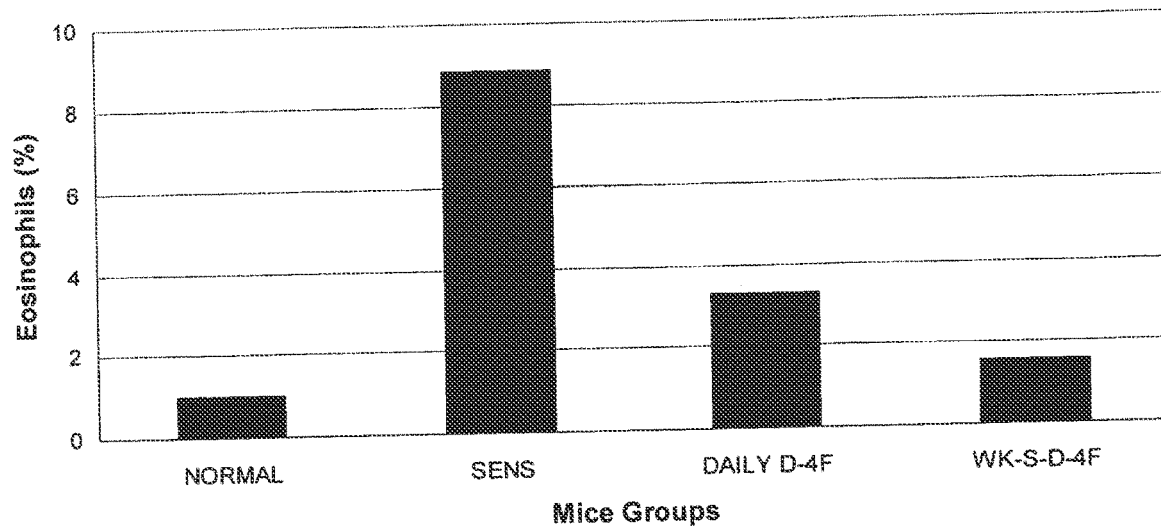
Figure 28:
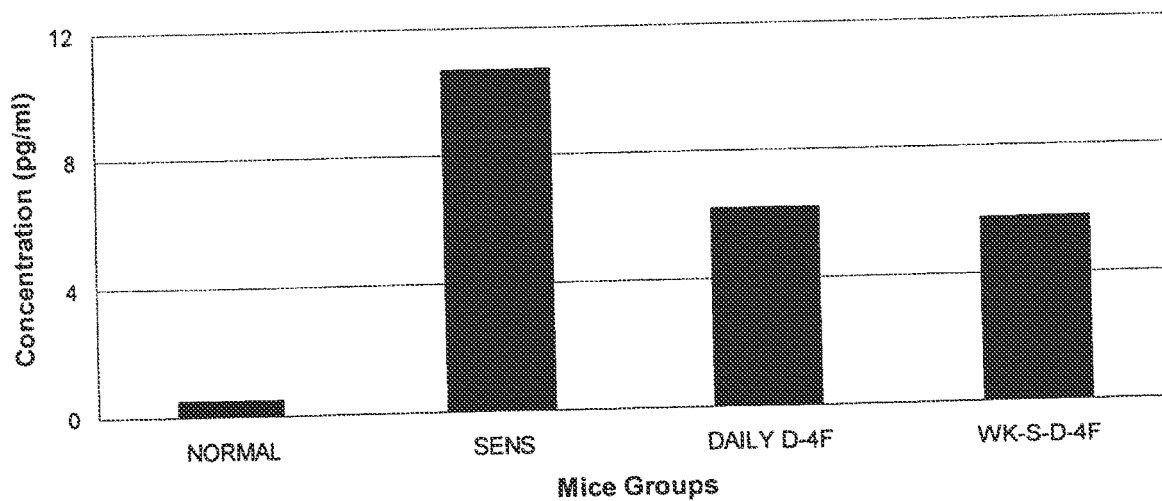
Figure 29:
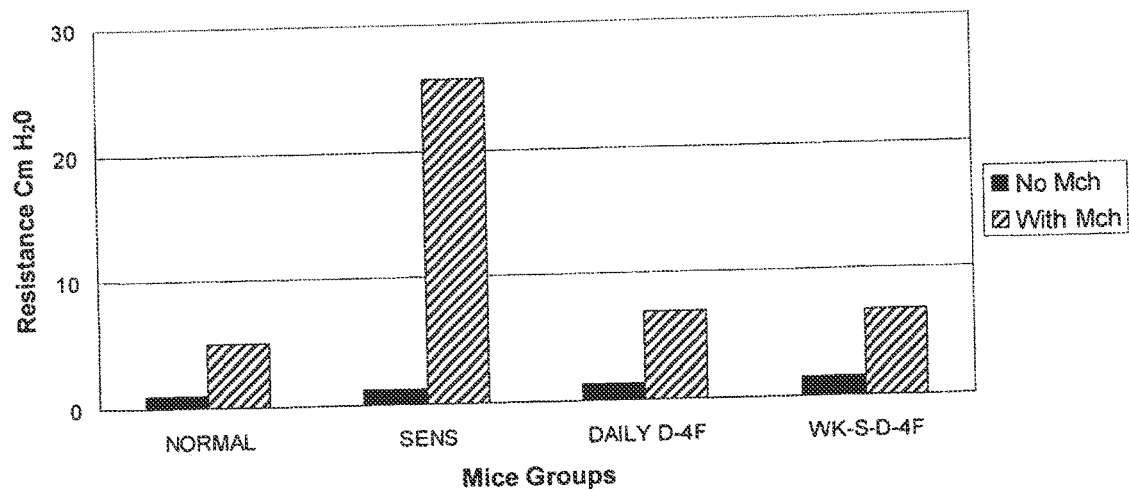
Figure 30:
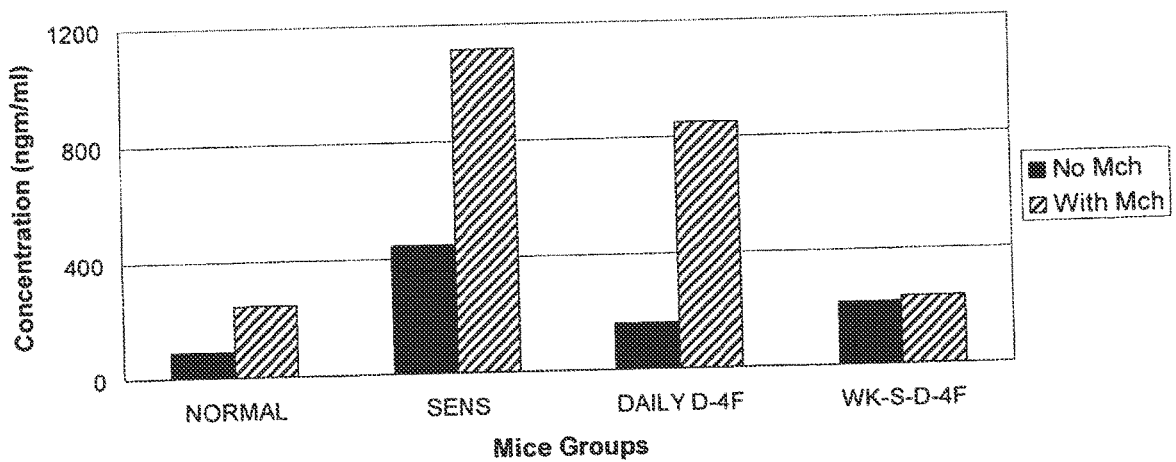
Figure 31:
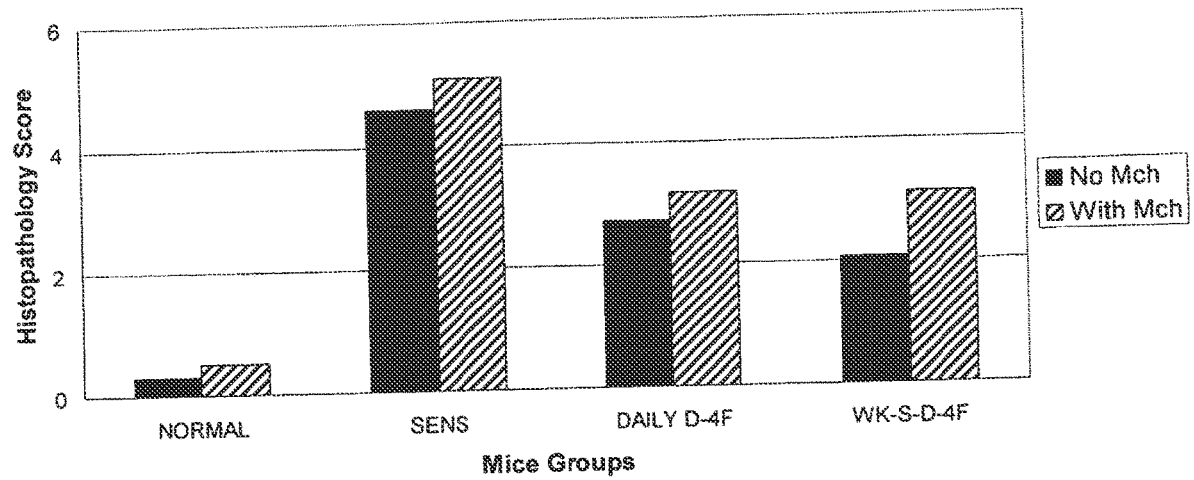

FIG. 24: Histopathology of the airway hyperreactivity (AHR) responses without and with Methacholine (Mch) challenge with D-4F treatment. Representative specimens are stained with hematoxylin-eosin are shown at a magnification of 100×. Top Row represents all groups without Mch challenge a) Normal b) SENS c) Dailey D-4F d) WK-S-D-4F. Bottom Row represents all groups with Mch challenge e) Normal 0 SENS g) Dailey D-4F h) WK-S-D-4F. The lung tissues from SENS group had persistent and significant inflammation compared to the NORMAL group with and without Mch challenge. There were significant decreases in lung inflammation in both the Dailey D-4F and WK-S-D-4F groups with and without Mch challenge.

|  | Histo (FIG. 25) | EPO (FIG. 26) | PB Eos (FIG. 27) | IgE levels (FIG. 28) |
|---|---|---|---|---|
| NORMAL | -- | -- | -- | -- |
| SENS | ↑ | ↑ | ↑ | ↑ |
| Daily D-4F | ↓ | ↓ | ↓ | ↓ |
| WK-S-D-4F | ↓ | ↓ | ↓ | ↓ |

|  | AHR to Mch (FIG. 29) | Histo (No Mch) (FIG. 30) | Histo (With Mch) (FIG. 31) | EPO (No Mch) (FIG. 31) | EPO (With Mch) (FIG. 31) |
|---|---|---|---|---|---|
| NORMAL | -- | -- | -- | -- | -- |
| SENS | ↑ | ↑ | ↑ | ↑ | ↑ |
| Daily D-4F | ↓ | ↓ | ↓ | ↓ | ↓ |
| WK-S-D-4F | ↓ | ↓ | ↓ | ↓ | ↓ |

| Legend | ↑ | Ø | ↓ | -- |
|---|---|---|---|---|
|  | Moderate-Severe inflammation | No significant reduction in inflammation | Significant reduction in inflammation | No inflammation |

Figure 32:
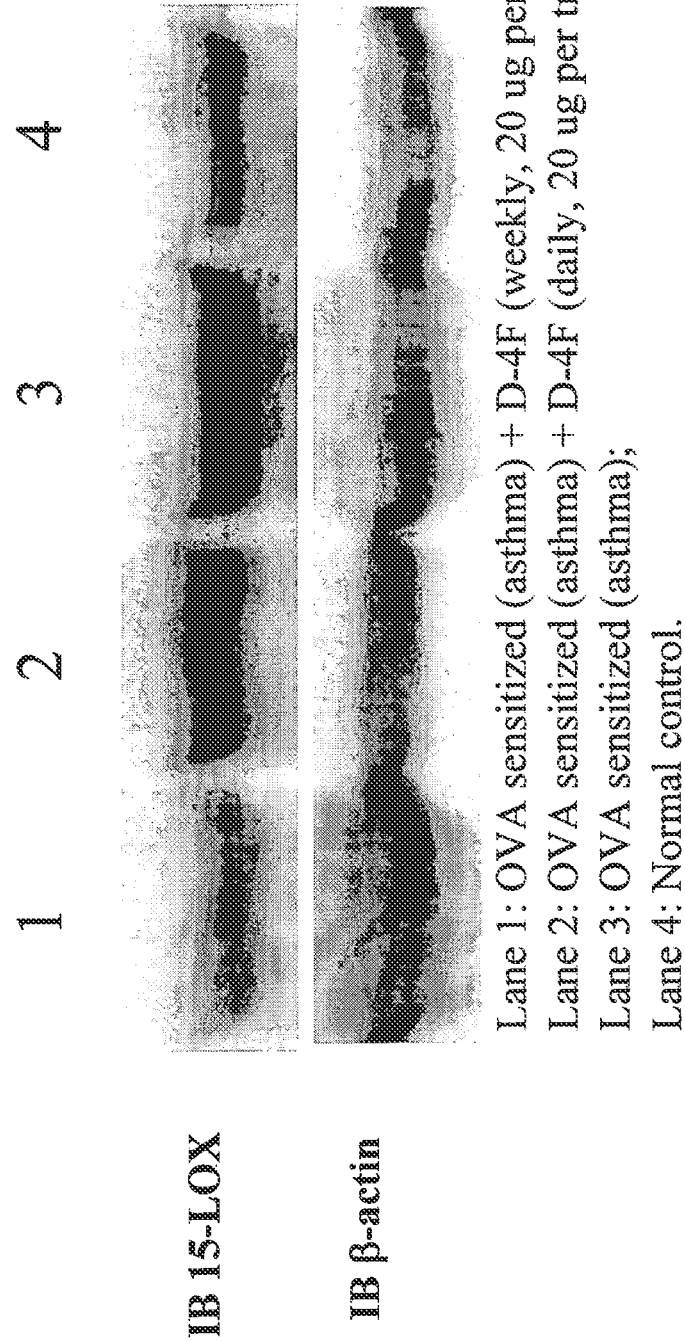
Figure 33:
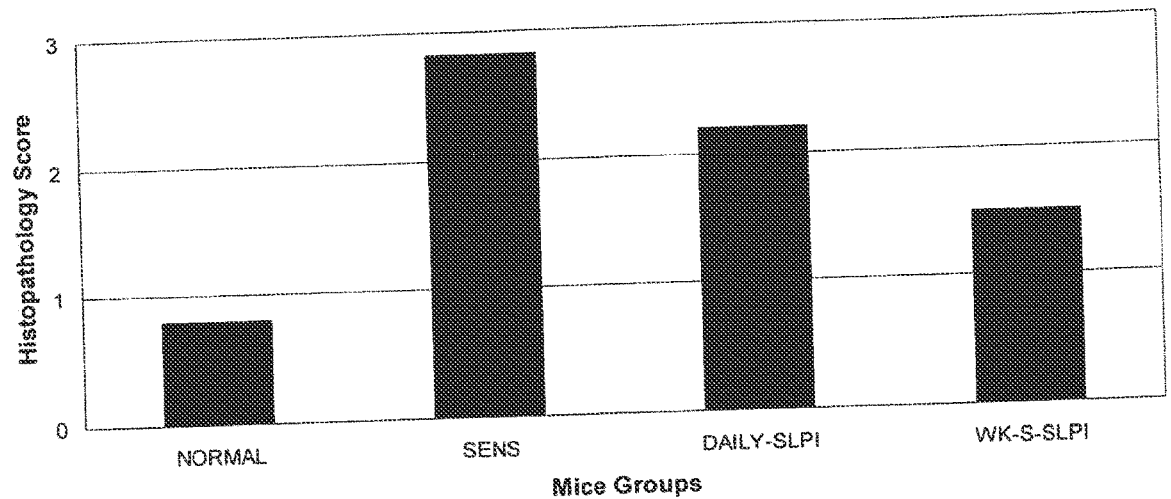
FIGS. 33-37 show graphical presentations of the use of SLPI encapsulated in the carrier on lung inflammation and AHR for the mice groups tested in SLIPI.
Figure 34:
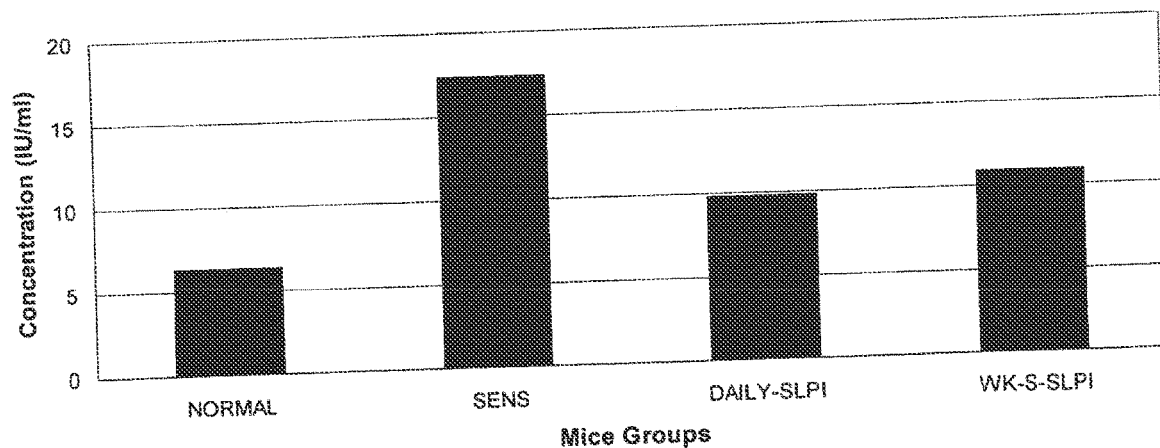
Figure 35:
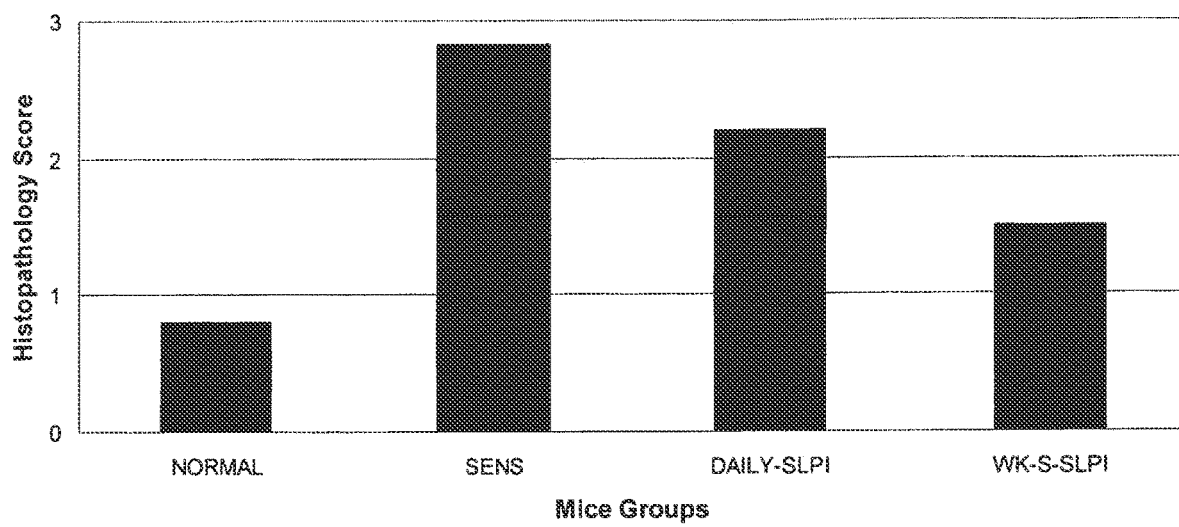
Figure 36:
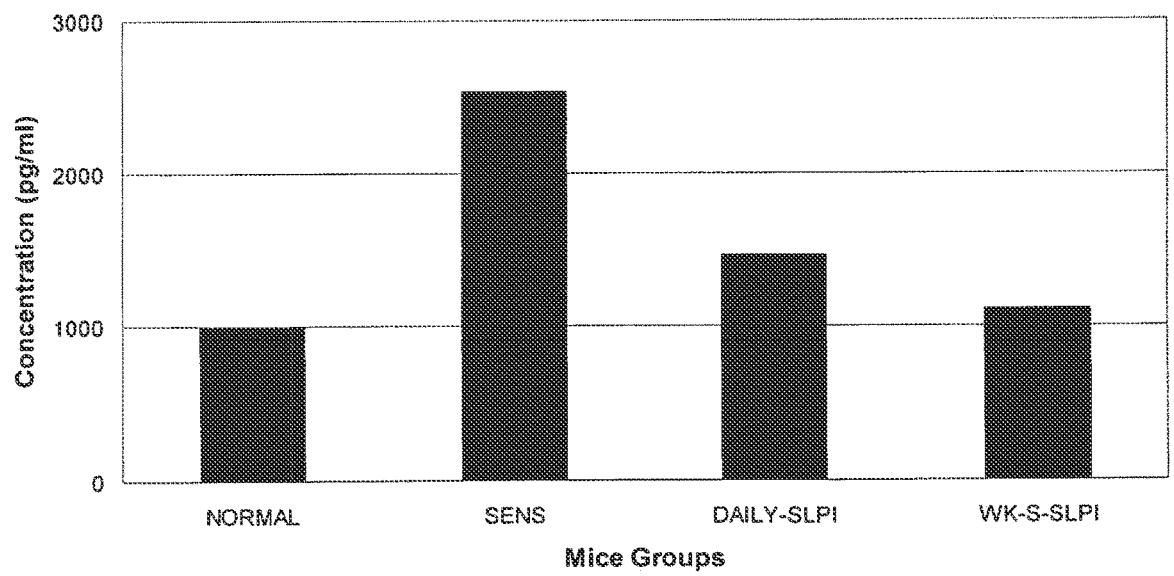
Figure 37:
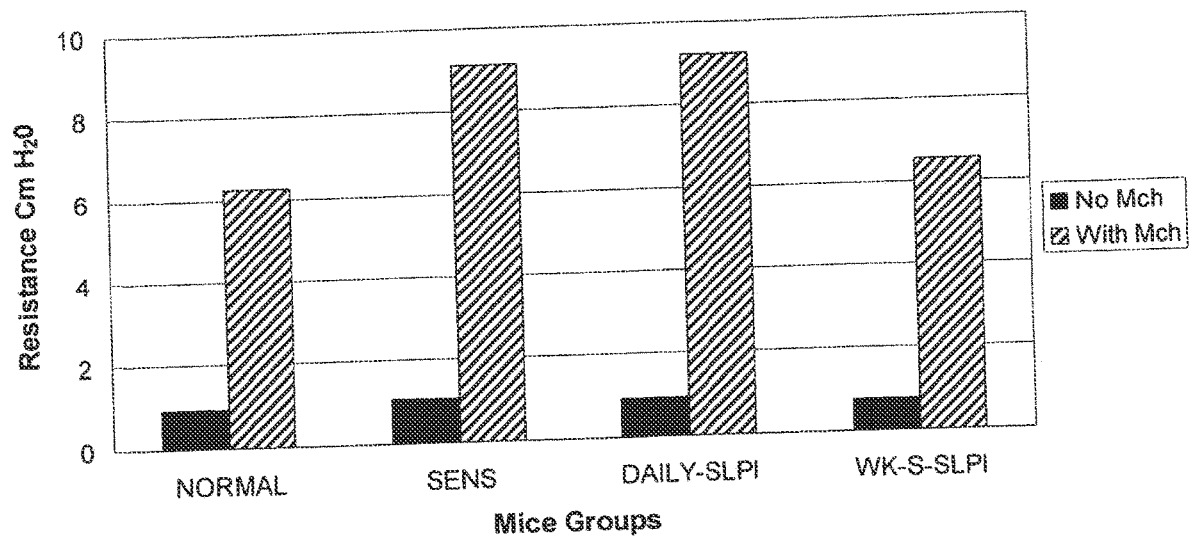

FIG. 32: Western Blot analysis performed on whole lung tissues and the Gel picture depicting the 15-lipooxygenase activity after treatment with D-4F are shown in this figure. The top row represents 15-lipooxygenase activity and the bottom row represents beta-actin which represents a control for the amount of protein extracted. Lane 1 represents sensitized mice treated with D-4F encapsulated in the carrier, given once a week. Lane 2 represents sensitized mice treated only D-4F without encapsulation in the carrier, given as a daily treatment. Lane 3 represents sensitized untreated mice used as a control. Lane 4 represents normal which are unsensitized and untreated. The intensity of the band for weekly treatment with D-4F encapsulated in the carrier (Lane 1) is significantly decreased and is comparable to the band that is found with the normal untreated, unsensitized mice (Lane 4), when compared to the untreated, sensitized mice (Lane 3). In comparison, the daily treatment with D-4F not encapsulated in the carrier (Lane 2) did not significantly decrease the intensity when compared to the untreated, unsensitized normal mice (Lane 4), or the untreated, sensitized mice (Lane 3).

SUMMARY: In the set of data given for D-4F, it was demonstrated that D-4F encapsulated in the Carrier with (WK-S-D-4F) given intranasally once a week, reduced lung inflammation, lung eosinophil peroxidase activity (EPO), serum IgE levels, and peripheral blood eosinophil counts, and airway hyperreactivity (AHR) to methacholine (Mch) challenge as effectively as the same dosage of D-4F given once a day intranasally (Daily D-4F) when compared to the Sensitized Untreated Asthmatic group (SENS) and was comparable to the NORMAL group.

SLPI: Effect of SLPI Encapsulated in the Carrier on Lung Inflammation and AHR (FIGS. 33-37)

SLPI: Treatment Groups

| | |
|---|---|
| NORMAL | Unsensitized, Untreated Normal mice |
| SENS | Senstitized, Untreated Asthmatic mice |
| Daily SLPI | 20 μg of SLPI without the Carrier given daily-Standard therapy |
| WK-S-SLPI | 20 μg of SLPI in the Carrier with Cholesterol given once a week |
| WK-ES | Buffer loaded empty, Carrier without drug, with Cholesterol given once a week |

SLPI: Results

| | Histo (FIG. 33) | EPO (FIG. 34) | PB Eos (FIG. 35) |
|---|---|---|---|
| NORMAL | -- | -- | -- |
| SENS | ↑ | ↑ | ↑ |
| Daily SLPI | ↓ | ↓ | ↓ |
| WK-S-SLPI | ↓ | ↓ | ↓ |
| WK-ES | ∅ | ∅ | ∅ |

| | IgE levels (FIG. 36) | AHR (FIG. 37) |
|---|---|---|
| NORMAL | -- | -- |
| SENS | ↑ | ↑ |
| Daily SLPI | ↓ | ∅ |
| WK-S-SLPI | ↓ | ↓ |
| WK-ES | ∅ | ∅ |

| Legend | ↑ | ∅ | ↓ | -- |
|---|---|---|---|---|
| | Moderate-Severe inflammation | No significant reduction in inflammation | Significant reduction in inflammation | No inflammation |

SUMMARY: In the set of data given for SLPI, it was demonstrated that SLPI encapsulated in the Carrier with (WK-S-SLPI) given once a week, reduced lung inflammation, lung eosinophil peroxidase activity (EPO), serum IgE levels, and peripheral blood eosinophil counts, and airway hyperreactivity (AHR) to methacholine (Mch) challenge as effectively as the same dosage of SLPI given once a day (Daily SLPI) when compared to the Sensitized Untreated Asthmatic group (SENS) and was comparable to the NORMAL group. Weekly treatments with Empty Carrier (WK-ES) did not have comparable effects on lung inflammation or AHR to Mch challenge.

Figure 39:
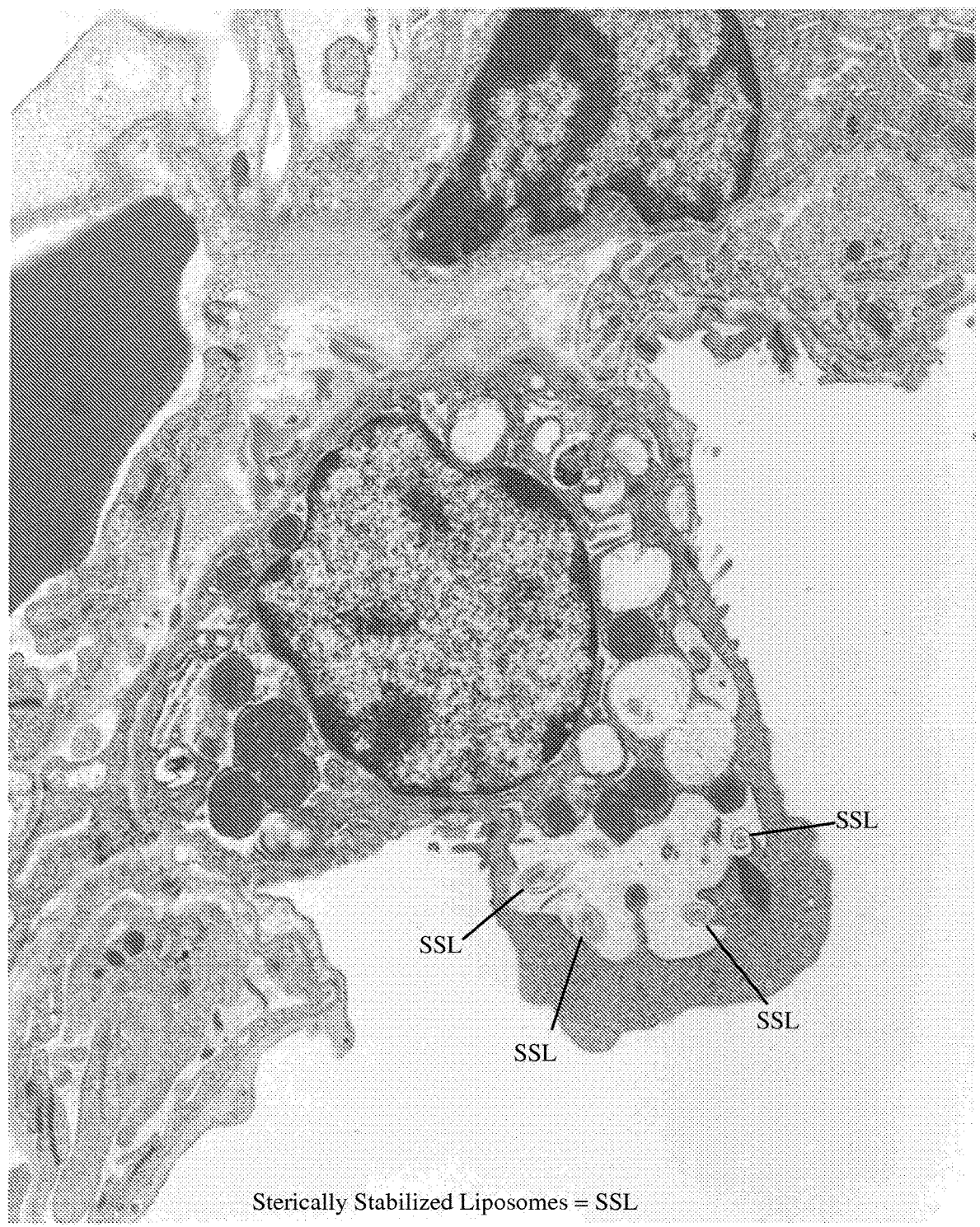

FIGS. 38-40: Electron Microscopy (EM) Studies of Lung Tissues, Transmission EM studies were obtained on the lung epithelium and airway cells. The large cell in the center is a Type II Pneumocytes which plays a critical role in surfactant production.

FIG. 38: Show EM of the lung epithelium of mice treated with budesonide encapsulated in conventional liposomes. The conventional liposomes encapsulated with budesonide are not detected anywhere in the lung epithelium or the airway cells. Magnification is ×5200.

FIG. 39: Shows EM of the lung tissues and cells on mice treated with the sterically stabilized carrier encapsulated with budesonide treated once a week. There are swirls of the sterically stabilized liposomes encapsulated with budesonide in the Type II Pneumocytes, as shown by arrows . . . Magnification is ×5200.

FIG. 40: Shows the same specimen as in FIG. 39 but with higher magnification. The micrograph shows higher magnification of the airway with Type II Pneumocytes with sterically stabilized liposomes encapsulated with budesonide. The swirls of the liposomes with drug are shown the type II Pneumocytes, as shown by arrows. Magnification is ×7200.

In the present study, it was demonstrated that one dose of BUD encapsulated in sterically stabilized liposomes, given once per week, reduced inflammation as effectively as the same dosage of BUD given once per day. Weekly treatments with only free BUD, BUD encapsulated in conventional liposomes and empty sterically stabilized liposomes did not have comparable effects.

While the present invention has been described by reference to certain of its preferred embodiments, it is pointed out that the embodiments described are illustrative rather than limiting in nature and that many variations and modifications are possible within the scope of the present invention. Many such variations and modifications may be considered obvious and desirable by those skilled in the art based upon a review of the foregoing descriptions of preferred embodiments.

The invention claimed is:

1. A method for treating lung inflammation or airway hyperreactivity, comprising:
    administering to a subject in need thereof an aerosol formulation or intranasal formulation comprising a drug in an amount that is therapeutically effective for treating lung inflammation or airway hyperreactivity,
    wherein the drug is encapsulated in a sterically stabilized liposome carrier comprising a phosphatidylcholine (PC), a phosphatidylglycerol (PG), and a poly (ethylene glycol) distearoylphosphatidyl ethanolamine (PEG-DSPE),
    wherein the aerosol formulation has a particulate size of more than 0.2 micrometers and up to 5 micrometers, and
    wherein the PC comprises synthetic palmitoyloleoyl-PG (POPC) and/or the PG comprises synthetic palmitoyloleoyl-PG (POPG), and wherein the sterically stabilized liposome carrier is free of cholesterol.

2. The method of claim 1, wherein the sterically stabilized liposome carrier comprises from about 20 to about 30 mole percent of the PG.

3. The method of claim 1, wherein the sterically stabilized liposome carrier comprises from about 1 to about 5 mole percent of the PEG-DSPE.

4. The method of claim 1, wherein the aerosol formulation comprises from about 1 to about 33 mole percent of the drug.

5. The method of claim 1, wherein the drug comprises a corticosteroid, monophosphoryl lipid A (MPL), D-4F (apol lipoprotein A-1 mimetic), Serine Lung Protease Inhibitor (SLPI), a bronchodilator, a leukotriene inhibitor, an antihistamine, or any combination thereof.

6. The method of claim 5, wherein the corticosteroid comprises budesonide, flunisolide, triamcinolone, beclomethasone, fluticasone, mometasone, dexamethasone, hydrocortisone, methylprednisolone, prednisone, cortisone, or betamethasone.

7. The method of claim 5, wherein the bronchodilator comprises terbutaline, albuterol, ipatropium, pirbuterol, epinephrine, salmeterol, levalbuterol, or formoterol.

8. The method of claim 5, wherein the leukotriene inhibitor comprises montelukast, zafirlukast, or zileuton.

9. The method of claim 5, wherein the antihistamine comprises loratadine or cetirizine.

10. The method of claim 1, wherein the drug comprises a steroid.

11. The method of claim 1, wherein the drug comprises budesonide (BUD), triamcinolone (TRI), monophosphoryl lipid A (MPL), apol lipoprotein A-1 mimetic (D-4F), serine lung protease inhibitor (SLPI), dexamethasone, a corticosteroid, or any combinations thereof.

12. The method of claim 1, wherein the aerosol formulation has an effective life of at least two days and up to two weeks in the subject after the administering.

13. The method of claim 1, wherein the aerosol formulation has an effective life of at least one week in the subject after the administering.

14. The method of claim 1, wherein the aerosol formulation has an effective life that is at least twice of an effective life of a corresponding formulation without the sterically stabilized liposome carrier, when administered to the subject.

15. The method of claim 1, wherein the administering produces a lower serum IgE concentration in the subject than a corresponding formulation without the sterically stabilized liposome carrier when given once a week.

16. The method of claim 1, wherein the method treats lung inflammation in the subject.

17. The method of claim 1, wherein the administering occurs once every 1 to 2 weeks.

* * * * *